(12) United States Patent
Yoshida et al.

(10) Patent No.: US 7,989,576 B2
(45) Date of Patent: Aug. 2, 2011

(54) TRIAZINE DERIVATIVE, LIQUID CRYSTAL COMPOSITION, ANISOTROPIC MATERIAL, AND LIQUID CRYSTAL DISPLAY DEVICE USING THE SAME

(75) Inventors: Aiko Yoshida, Minami-ashigara (JP); Hiroshi Takeuchi, Minami-ashigara (JP)

(73) Assignee: Fujifilm Corporation, Tokyo (JP)

( * ) Notice: Subject to any disclaimer, the term of this patent is extended or adjusted under 35 U.S.C. 154(b) by 598 days.

(21) Appl. No.: 12/039,348

(22) Filed: Feb. 28, 2008

(65) Prior Publication Data

US 2009/0018305 A1 Jan. 15, 2009

(30) Foreign Application Priority Data

Mar. 5, 2007 (JP) ................. 2007-053967

(51) Int. Cl.
*C08G 73/00* (2006.01)
*C07D 251/54* (2006.01)
(52) U.S. Cl. ........ 528/289; 528/288; 544/193; 544/197; 252/299.01; 252/299.5
(58) Field of Classification Search .................. 528/289, 528/288; 544/197, 193; 252/299.01, 299.5
See application file for complete search history.

(56) References Cited

U.S. PATENT DOCUMENTS 6,338,808 B1 * 1/2002 Kawata et al. ............. 252/299.4
2006/0068997 A1 3/2006 Negoro et al.

FOREIGN PATENT DOCUMENTS

JP 2006-89672 A 4/2006

* cited by examiner

*Primary Examiner* — Duc Truong
(74) *Attorney, Agent, or Firm* — Birch, Stewart, Kolasch & Birch, LLP

(57) ABSTRACT

A triazine derivative represented by formula (I) below:

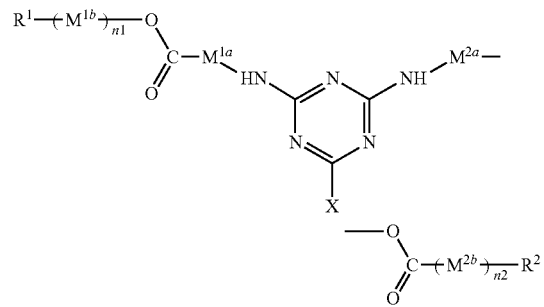

Formula (I)

where, in formula (I), each of $M^{1a}$, $M^{1b}$, $M^{2a}$ and $M^{2b}$ is a divalent group comprising one or more substituted or non-substituted aromatic rings; each of n1 and n2 is 0 or 1; each of $R^1$ and $R^2$ represents a hydrogen atom or substituent; and X represents a substituent; is disclosed.

10 Claims, No Drawings

TRIAZINE DERIVATIVE, LIQUID CRYSTAL COMPOSITION, ANISOTROPIC MATERIAL, AND LIQUID CRYSTAL DISPLAY DEVICE USING THE SAME

CROSS-REFERENCE TO RELATED APPLICATIONS

This application claims benefit of priority under 35 U.S.C. 119 to Japanese Patent Application No. 2007-053967 filed Mar. 5, 2007, and the entire contents of the applications are incorporated herein by reference.

BACKGROUND OF THE INVENTION

1. Field of the Invention

The present invention relates to a novel triazine derivative, and further to a liquid crystal composition containing the triazine derivative, an anisotropic material produced by fixing alignment of the liquid crystal composition, and a liquid crystal display device comprising the anisotropic material.

2. Related Art

Liquid crystal materials are employed for producing anisotropic materials in various fields. For example, optical compensation elements having an optically anisotropic layer produced by using liquid crystal materials are employed in liquid crystal display devices of various display modes, for the purpose of canceling coloration of images, and of widening the viewing angles.

In producing an anisotropic material by using a low-molecular-weight liquid crystal, generally, a liquid crystal composition is transferred into a predetermined liquid crystal phase, and then fixed the alignment state. The main stream of the conventional method was such as aligning the liquid crystal material in the nematic phase which is the lowest in the order degree among various liquid crystal phases, and then fixing the alignment. The anisotropic material may, however, cause non-uniformity in the characteristics, and may fail in satisfying required characteristics, due to thermal fluctuation of the nematic phase. For example, a liquid crystal display device comprising an optical compensation element made of the fixed nematic phase may cause leakage of light in the black state, and may fail in satisfying demands for higher image quality, in particular, higher contrast. Aiming at solving this problem, there have been proposed techniques of producing the anisotropic material made of the fixed smectic phase characterized by its smaller thermal fluctuation. Known liquid crystal materials, however, suffer from non-conformities on the producing basis, including too high in the phase transition temperature to the smectic phase, or insufficient solubility into solvent for preparing a coating liquid, and need some improvement.

On the other hand, triazine derivatives having a triazine ring have been employed in various fields, wherein only a few knowledge on the liquid crystallinity, in particular expression performance of smectic phase, has been available (Japanese Laid-Open Patent Publication, referred to as "JPA", No. 2006-89672).

SUMMARY OF THE INVENTION

It is therefore an object of the present invention to provide a novel triazine derivative and a liquid crystal composition, useful for producing anisotropic materials in the various fields, including manufacturing of optical compensation elements.

It is another object of the present invention to provide an anisotropic material useful typically as optical compensation elements of liquid crystal display devices, and a liquid crystal display device employing such anisotropic material, and therefore excellent in the display performance.

In one aspect, the present invention provides a triazine derivative represented by formula (I) below:

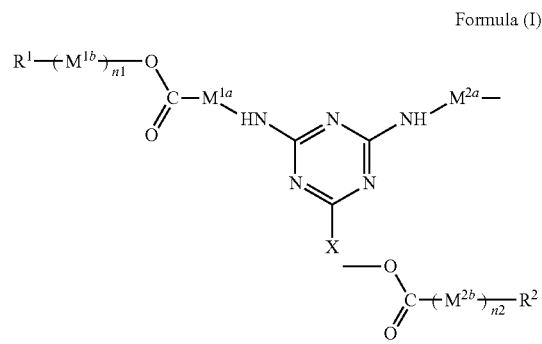

Formula (I)

where, in formula (I), each of $M^{1a}$, $M^{1b}$, $M^{2a}$ and $M^{2b}$ is a divalent group comprising one or more substituted or non-substituted aromatic rings; each of n1 and n2 is 0 or 1; each of $R^1$ and $R^2$ represents a hydrogen atom or substituent; and X represents a substituent.

As an embodiment of the invention, there is provided the triazine derivative represented by formula (II) below:

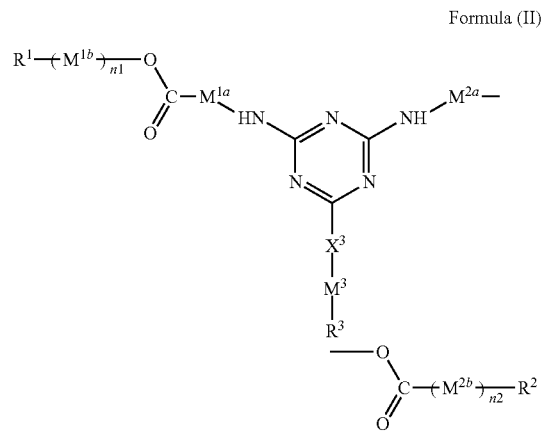

Formula (II)

where, in formula (II), $X^3$ represents a single bond, NH, S or O; $M^3$ is a divalent group comprising one or more substituted or non-substituted aromatic rings; $R^3$ represents a substituent; each of $M^{1a}$, $M^{1b}$, $M^{2a}$, $M^{2b}$, n1, n2, $R^1$ and $R^2$ is synonymous with each of those in formula (I);

In the formulae, each of $M^{1a}$, $M^{2a}$ and $M^3$ may be a group comprising at least one substituted or non-substituted 1,4-phenylene group.

In the formula, each of n1 and n2 may be 1, and each of $M^{1b}$ and $M^{2b}$ may be a group comprising at least one substituted or non-substituted 1,4-phenylene group.

In the formulae, each of $R^1$ and $R^2$ may comprise a polymerizable group represented by any of formulae (Q-101) to (Q-106) below:

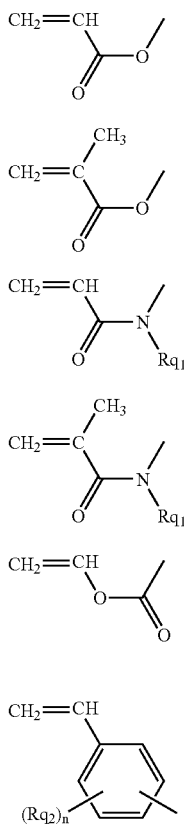

(Q-101)

(Q-102)

(Q-102)

(Q-104)

(Q-105)

(Q-106)

where, in the formulae, $Rq_1$ is a hydrogen atom, alkyl group, or aryl group; $Rq_2$ is a substituent; and n is an integer from 0 to 4.

In formula (I), X may be $-NH-M^{1a}-C(=O)O-(M^{1b})_{n1}-R^1$ or $NH-M^{2a}-OC(=O)-(M^{2b})_{n2}-R^2$.

As an embodiment of the invention, there is provided the triazine derivative represented by formula (III) below:

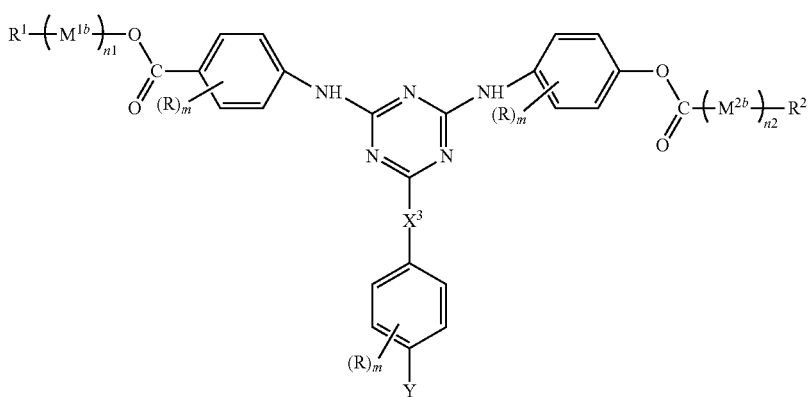

Formula (III)

where, in the formula, each of $M^{1b}, M^{2b}, R^1, R^2$, n1 and n2 is synonymous with each of those in formula (I); $X^3$ represents a single bond, NH, S or O; each of Y and R represents a substituent; each m represents an integer from 0 to 4; and each of a plurality of (R)s and (m)s may be same with or different from each other.

In formula (III), Y may be either of the formulae below;

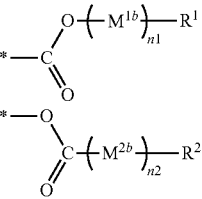

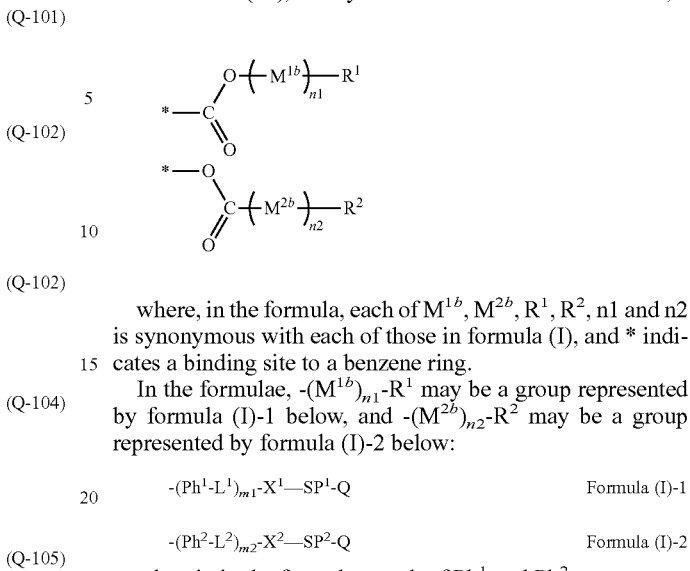

where, in the formula, each of $M^{1b}, M^{2b}, R^1, R^2$, n1 and n2 is synonymous with each of those in formula (I), and * indicates a binding site to a benzene ring.

In the formulae, $-(M^{1b})_{n1}-R^1$ may be a group represented by formula (I)-1 below, and $-(M^{2b})_{n2}-R^2$ may be a group represented by formula (I)-2 below:

$-(Ph^1-L^1)_{m1}-X^1-SP^1-Q$  Formula (I)-1

$-(Ph^2-L^2)_{m2}-X^2-SP^2-Q$  Formula (I)-2 wherein in the formulae, each of $Ph^1$ and $Ph^2$ represents a substituted or non-substituted 1,4-phenylene group; $L^1$ represents a single bond or #—C(=O)O— (# indicates a binding site to $Ph^1$); $L^2$ represents a single bond or #—OC(=O)— (# indicates a binding site to $Ph^2$); each of m1 and m2 is an integer from 1 to 3, and each of m1 ($Ph^1-L^1$)s and m2 ($Ph^2-L^2$)s may be same with or different from each other; each of $SP^1$ and $SP^2$ represents a spacer group comprising a chain structure having four or more atoms; each of $X^1$ and $X^2$ represents a single bond or divalent linking group; and Q represents any of the polymerizable groups represented by formulae (Q-101) to (Q-106).

The triazine derivative may have liquid crystallinity, and preferably a smectic phase.

In another aspect, the present invention provides a liquid crystal composition comprising at least one triazine derivative of the invention; an anisotropic material formed by curing the liquid crystal composition; and a liquid crystal display device comprising the anisotropic material.

DETAILED DESCRIPTION OF THE INVENTION

Details of the present invention will be explained below step by step. It is to be understood that all numerical ranges expressed using "to" in this patent specification mean ranges including the numerical values placed therebefore and thereafter as the lower limit and upper limit, respectively.

[Triazine Derivative]

The present invention relates to a triazine derivative represented by formula (I).

Formula (I)

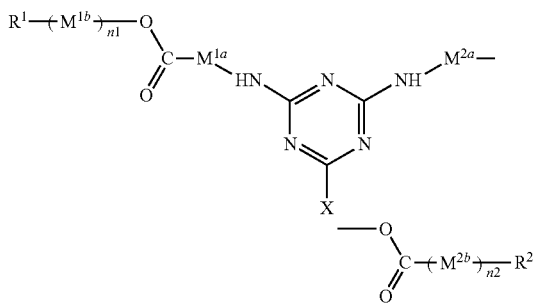

In formula (I), each of $M^{1a}$, $M^{1b}$, $M^{2a}$, $M^{2a}$ and $M^{2b}$ is a divalent group containing one or more substituted or non-substituted aromatic rings; each of n1 and n2 is 0 or 1; each of $R^1$ and $R^2$ represents a hydrogen atom or substituent; and X represents a substituent.

The aromatic ring in each of $M^{1a}$, $M^{1b}$, $M^{2a}$ and $M^{2b}$ may be a monocycle or condensed ring. It may also be a hydrocarbon-base aromatic ring having only carbon atoms as the ring-composing atoms, or may be a heteroatom-base aromatic ring having at least one species of hetero atom, other than carbon atom, as the ring-composing atoms. These rings may have one or more substituents, wherein examples of the substituent may include a group G of substituents described later. Among those, F, Cl, Br, CN, $NO_2$, $CH_3$, $C_2H_5$, $OCH_3$, $OC_2H_5$, $COCH_3$, $COC_2H_5$, $CF_3$, $OCF_3$, $OCHF_2$, and $OC_2F_5$ are preferable as the substituent on the aromatic ring; F, Er, Cl, CN, $CH_3$, $C_2H_5$, $OCH_3$, $COCH_3$ and $OCF_3$ are more preferable; and F, Br, $CH_3$, $OCH_3$ and $COCH_3$ are still more preferable.

In formula (I) in the above, each of $M^{1a}$ and $M^{2a}$ is preferably a divalent group having a benzene ring, more preferably a substituted or non-substituted phenylene group, and still more preferably a substituted or non-substituted 1,4-phenylene group.

Each of $M^{1b}$ and $M^{2b}$ is preferably a divalent group having one or more benzene rings.

Each of $M^{1a}$, $M^{1b}$, $M^{2a}$ and $M^{2b}$ may alternatively be a divalent group having a partial structure containing a plurality of rings, which is so-called "mesogen". The triazine derivative of the present invention is, however, not limited to compounds showing liquid crystallinity.

In formula (I) in the above, each of -$(M^{1b})_{n1}$-OC(=O)-$M^{1a}$ and -$(M^{2b})_{n2}$-C(=O)O-$M^{2a}$ preferably has a divalent group represented by formula MG-I below:

-(A$^1$-Z$^1$)$_m$-A$^2$-Z$^2$-A$^3$-  Formula MG-I where, in formula MG-I, each of $A^1$, $A^2$ and $A^3$ is 1,4-phenylene group, heterocyclic group having one or two or more of the CH groups thereof substituted by N, 1,4-cyclohexylene group, heterocyclic group having one $CH_2$ group or two non-adjacent $CH_2$ groups of 1,4-cyclohexylene group possibly substituted by O and/or S, 1,4-cyclohexenylene group, or naphthalene-2,6-diyl group. These groups may have one or more substituents. Examples of the substituents include those in a group G of substituents described later.

In formula MG-I, each of $Z^1$ and $Z^2$ is —COO—, —OCO—, —$CH_2CH_2$—, —$OCH_2$—, —$CH_2O$—, —CH=CH—, —C≡C—, —CH=CH—COO—, —OCO—CH=CH— or single bond; and is more preferably —COO—, —OCO—, —$CH_2$—$CH_2$—, —CH=CH—COO—, —OCO—CH=CH— or single bond. The ester group (COO) contains two types such as —OC(=O)— and —C(=O)O—, based on difference in the order of bonds. In the embodiments where $Z^1$ and $Z^2$ in $M^{1b}$ is an ester group, such ester group preferably has the order of bonds same with that of the ester group which resides between $M^{1a}$ and $M^{1b}$, and similarly in the embodiments where $Z^1$ and $Z^2$ in $M^{2b}$ is an ester group, such ester group preferably has the order of bonds same with that of the ester group which resides between $M^{2a}$ and $M^{2b}$. More specifically, in the embodiments where there is one or more ester groups in $M^{1b}$, all ester groups may preferably be *—C(=O)O— (* indicates a binding site to the $M^{1a}$ side), and in the embodiments where there is one or more ester groups in $M^{2b}$, all ester groups may preferably be *—OC(=O)— (* indicates a binding site to the $M^{2a}$ side). Compounds satisfying these conditions may be a liquid crystal compound having a higher degree of order, more likely to align, that is, capable of causing transition to smectic phase at an appropriate temperature.

In formula MG-I, m is 0, 1 or 2.

Preferable examples of the divalent group represented by formula MG-I are shown below. It is to be noted that the examples below are shown using abbreviations for simplicity, wherein Phe represents 1,4-phenylene, "PheL" represents phenylene substituted by at least one substituent L, and "Cyc" represents 1,4-cyclohexylene.

| | |
|---|---|
| -Phe-Z$^2$-Phe- | II-1 |
| -Phe-Z$^2$-Cyc- | II-2 |
| -PheL-Z$^2$-Phe- | II-3 |
| -PheL-Z$^2$-Cyc- | II-4 |
| -Phe-Z$^2$-PheL- | II-5 |
| -Phe-Z$^1$-Phe-Phe- | II-6 |
| -Phe-Z$^1$-Phe-Cyc- | II-7 |
| -Phe-Z$^1$-Phe-Z$^2$-Phe- | II-8 |
| -Phe-Z$^1$-Phe-Z$^2$-Cyc- | II-9 |
| -Phe-Z$^1$-Cyc-Z$^2$-Phe- | II-10 |
| -Phe-Z$^1$-Cyc-Z$^2$-Cyc- | II-11 |
| -Phe-Z$^1$-PheL-Z$^2$-Phe- | II-12 |
| -Phe-Z$^1$-Phe-Z$^2$-PheL- | II-13 |
| -PheL-Z$^1$-Phe-Z$^2$-PheL- | II-14 |
| -PheL-Z$^1$-PheL-Z$^2$-Phe- | II-15 |
| -PheL-Z$^1$-PheL-Z$^2$-PheL- | II-16 |

In these formulae, each of $Z^1$ and $Z^2$ is preferably —COO—, —OCO—, —$CH_2CH_2$—, —CH=CH—COO— or single bond.

The divalent groups particularly preferable as the partial structures of formula MG-I are shown below. The divalent group represented by formula MG-I may be composed only of the divalent groups shown below, or may be any groups containing these groups. Either binding site may be bound to the triazine ring side, wherein these structures are preferably bound so that the order of bonds of ester groups agree with each other, as described in the above.

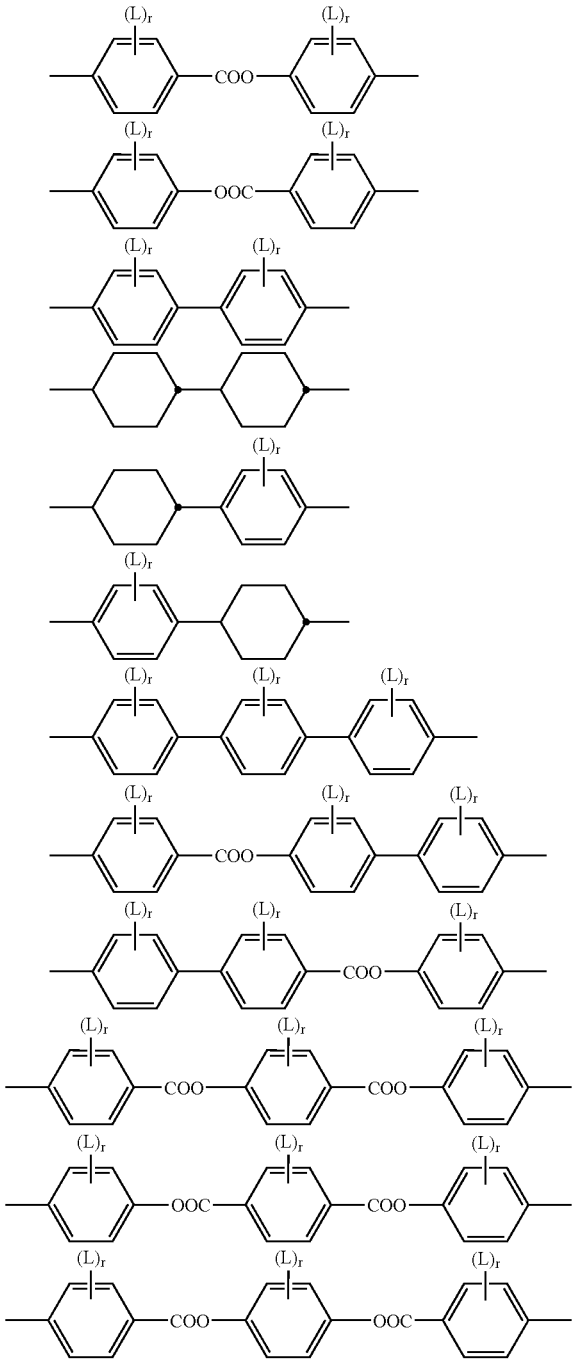

In the formulae, r represents an integer from 0 to 4, and is preferably 0, 1 or 2. When r is 2, two (L)s may be same with or different from each other.

In the formulae, L represents a substituent. Examples of the substituent may be those in a group G of substituents described later. Among those, preferable examples of the substituent L include halogen atom, cyano, nitro, alkyl group having 1 to 5 carbon atoms, halogen-substituted alkyl group having 1 to 5 carbon atoms, alkoxy group having 1 to 5 carbon atoms, alkylthio group having 1 to 5 carbon atoms, acyl group having 1 to 5 carbon atoms, acyloxy group having 2 to 6 carbon atoms, alkoxycarbonyl group having 2 to 6 carbon atoms, carbamoyl, alkyl-substituted carbamoyl group having 2 to 6 carbon atoms, and amido group having 2 to 6 carbon atoms. More preferable examples of the substituent L include halogen atom, cyano, alkyl group having 1 to 3 carbon atoms, halogen-substituted alkyl group having 1 to 3 carbon atoms, alkoxy group having 1 to 3 carbon atoms, and acyloxy group having 2 to 4 carbon atoms. Still more preferable examples of substituent L include F, Cl, Br, CN, $NO_2$, $CH_3$, $C_2H_5$, $OCH_3$, $OC_2H_5$, $COCH_3$, $COC_2H_5$, $CF_3$, $OCF_3$, $OCHF_2$, and $OC_2F_5$; further preferable examples include F, Br, Cl, CN, $CH_3$, $C_2H_5$, $OCH_3$, $COCH_3$ and $OCF_3$; and still further preferable examples include F, Br, $CH_3$, $OCH_3$ and $COCH_3$.

In the formula, each of $M^{1b}$ and $M^{2b}$ more preferably contains a divalent group represented by formula MG-II below:

$$-(Phe-Z)_m- \quad \text{Formula MG-II}$$

In the formula, "Phe" is 1,4-phenylene group which may have a substituent. Examples of the substituent may be those in a group G of substituents described later. Z is a linking group or single bond, and m is an integer from 1 to 3.

Preferable examples of the linking group represented by Z include —COO—, —OCO—, —$CH_2CH_2$—, —$OCH_2$—, —$CH_2O$—, —CH=CH—, —C≡C—, —CH=CH—COO—, —OCO—CH=CH— and single bond; more preferable examples include —COO—, —OCO—, —$CH_2$—$CH_2$—, —CH=CH—COO—, —OCO—CH=CH— and single bond; and still more preferable examples include —COO—, —OCO—, and single bond.

One example of the triazine derivative of the present invention is a compound wherein $-(M^{1b})_{n1}-R^1$ is a group represented by formula (I)-1 below, and that $-(M^{2b})_2-R^2$ is a group represented by formula (I)-2 below. The triazine derivative may be aligned with a higher level of order, and may express the smectic phase within appropriate temperature ranges:

$$-(Ph^1-L^1)_{m1}-X^1-SP^1-Q \quad \text{Formula (I)-1}$$

$$-(Ph^2-L^2)_{m2}-X^2-SP^2-Q \quad \text{Formula (I)-2}$$

In the formulae, each of $Ph^1$ and $Ph^2$ represents a substituted or non-substituted 1,4-phenylene group; $L^1$ represents a single bond or #—C(=O)O— (# indicates a binding site to $Ph^1$); $L^2$ represents #-OC(=O)— (# indicates a binding site to $Ph^2$); each of n1 and n2 is 0 or 1, each of m1 and m2 is an integer from 1 to 3, m1 ($Ph^1$-$L^1$)s and m2 ($Ph^2$-$L^2$)s may be same with or different from each other; each of $SP^1$ and $SP^2$ represents a spacer group containing a chain structure having 4 or more atoms; each of $X^1$ and $X^2$ represents a single bond or divalent linking group; and Q represents a polymerizable group.

Each of $SP^1$ and $SP^2$ is a spacer group containing a chain structure having 4 or more atoms, and is preferably a spacer group selected from the group consisting of —O—, —S—, —CO—, —$NR^a$—, divalent chain group, and combinations of them. $R^a$ is an alkyl group having 1 to 7 carbon atoms, or hydrogen atom.

The divalent chain group means alkylene group, substituted alkylene group, alkenylene group, substituted alkenylene group, alkynylene group or substituted alkynylene group, preferably means alkylene group, substituted alkylene group, alkenylene group and substituted alkenylene group, and still more preferably means alkylene group and alkenylene group. The alkylene group may be branched. The alkylene group preferably has 1 to 12 carbon atoms, more preferably has 2 to 10 carbon atoms, and still more preferably has 2 to 8 carbon atoms. The alkylene portion of the substituted alkylene group is same as that of the alkylene group described in the above. Examples of substituent of the substituted alkylene group include alkoxy group and halogen atom. The alkenylene group may be branched. The alkenylene group preferably has 2 to 12 carbon atoms, more preferably has 2 to 10 carbon atoms, and still more preferably has 2 to 8 carbon atoms. Alkenylene portion of the substituted alkenylene group is same as that of the alkenylene group described in the above. Examples of substituent of the substituted alkenylene group include alkoxy group and halogen atom. The alkynylene group may be branched. The alkynylene group preferably has 2 to 12 carbon atoms, more preferably has 2 to 10 carbon atoms, and still more preferably has 2 to 8 carbon atoms. Alkynylene portion of the substituted alkynylene group is same as that of the alkynylene group described in the above. Examples of substituent of the substituted alkynylene group include alkoxy group and halogen atom. In the divalent chain group, one or more non-adjacent $CH_2$ group may be substituted by —O—, —CO—O—, —O—CO—, —O—CO—O—, —CO—, or —S—. The total number of carbon atoms of the spacer group is preferably 4 to 30, and is more preferably 4 to 20.

Preferable examples of $SP^1$ and $SP^2$ include those shown below, but are not limited thereto. In the specific examples below, "*" indicates a binding site to $R^1$ or $R^2$.

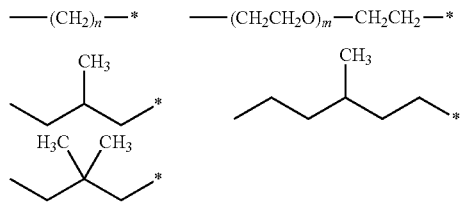

In the formulae, each of n and m represents an integer of 1 or larger; n is preferably an integer from 1 to 20, and is more preferably an integer from 2 to 10; and m is an integer from 1 to 10, and is more preferably an integer from 1 to 6.

Each of $X^1$ and $X^2$ represents a single bond or divalent linking group, and preferably represents a divalent linking group selected from the group consisting of —O—, —S—, —CO—, —NR— (R is a hydrogen atom, alkyl group, and aryl group, preferably a hydrogen atom, alkyl group having 1 to 5 carbon atoms, aryl group having 6 to 12 carbon atoms, more preferably a hydrogen atom, alkyl group having 1 to 3 carbon atoms, and still more preferably a hydrogen atom or methyl group), and combinations of them. More preferable examples include single bond, —O—, —C(=O)—O—, —O—C(=O)—, —CO—NH—, —NH—CO— and O—CO—O—.

Q represents a polymerizable group, and is preferably any of those represented by formulae (Q-101) to (Q-106) described later.

In formula (I), Examples of the substituent represented by $R^1$, $R^2$ or X include Substituent Group G.

Substituent Group G Includes halogen atoms such as fluorine, chlorine, bromine and iodine atoms; alkyls (preferably $C_{1-30}$ alkyls) such as methyl, ethyl, n-propyl, iso-propyl, tert-butyl, n-octyl, and 2-ethylhexyl; cylcoalkyls (preferably $C_{3-30}$ substituted or non-substituted cycloalkyls) such as cyclohexyl, cyclopentyl and 4-n-dodecylcyclohexyl; bicycloalkyls (preferably $C_{5-30}$ substitute or non-substituted bicycloalkyls, namely monovalent residues formed from $C_{5-30}$ bicycloalkanes from which a hydrogen atom is removed) such as bicyclo[1,2,2]heptane-2-yl and bicyclo[2,2,2]octane-3-yl; alkenyls (preferably $C_{2-30}$ alkenyls) such as vinyl and allyl; cycloalkenyls (preferably $C_{3-30}$ substituted or non-substituted cycloalkenyls, namely monovalent residues formed from $C_{3-30}$ cycloalkenes from which a hydrogen atom is removed) such as 2-cyclopentene-1-yl and 2-cyclohexene-1-yl; bicycloalkenyls (preferably $C_{5-30}$ substituted or non-substituted bicycloalkenyls, namely monovalent residues formed from $C_{5-30}$ bicycloalkenes from which a hydrogen atom is removed) such as bicyclo[2,2,1]hepto-2-en-1-yl and bicyclo[2,2,2]octo-2-en-4-yl; alkynyls (preferably $C_{2-30}$ substitute or non-substituted alkynyls) such as etynyl and propargyl; aryls (preferably $C_{6-30}$ substitute or non-substituted aryls) such as phenyl, p-tolyl and naphthyl; heterocyclic groups (preferably (more preferably $C_{3-30}$) substituted or non-substituted, 5-membered or 6-membered, aromatic or non-aromatic heterocyclic monovalent residues) such as 2-furyl, 2-thienyl, 2-pyrimidinyl and 2-benzothiazolyl; cyano, hydroxyl, nitro, carboxyl, alkoxys (preferably $C_{1-30}$ substituted or non-substituted alkoxys) such as methoxy, ethoxy, iso-propoxy, tert-butoxy, n-octyloxy and 2-methoxyethoxy; aryloxys (preferably $C_{6-30}$ substituted or non-substituted aryloxys) such as phenoxy, 2-methylphenoxy, 4-tert-butylphenoxy, 3-nitrophenoxy and 2-tetradecanoyl aminophenoxy; silyloxys (preferably $C_{3-20}$ silyloxys) such as trimethylsilyloxy and tert-butyldimethylsilyloxy; hetero-cyclic-oxys (preferably $C_{2-30}$ substituted or non-substituted hetero-cyclic-oxys) such as 1-phenyltetrazole-5-oxy and 2-tetrahydropyrenyloxy; acyloxys (preferably $C_{2-30}$ substitute or non-substituted alkylcarbonyloxys and $C_{6-30}$ substituted or non-substituted arylcarbonyloxys) such as formyloxyr acetyloxy, pivaloyloxy, stearoyoxy, benzoyloxy and p-methoxyphenylcarbonyloxy; carbamoyloxys (preferably $C_{1-30}$ substituted or non-substituted carbamoyloxys) such as N,N-dimethyl carbamoyloxy, N,N-diethyl carbamoyloxy, morpholinocarbonyloxy, N,N-di-n-octylaminocarbonyloxy and N-n-octylcarbamyloxy; alkoxy carbonyloxys (preferably $C_{2-30}$ substituted or non-substituted alkoxy carbonyloxys) such as methoxy carbonyloxy, ethoxy carbonyloxy, tert-butoxy carbonyloxy and n-octyloxy carbonyloxy; aryloxy carbonyloxys (preferably $C_{7-30}$ substituted or non-substituted aryloxy carbonyloxys) such as phenoxy carbonyloxy, p-methoxyphenoxy carbonyloxy and p-n-hexadecyloxyphenoxy carbonyloxy; aminos (preferably $C_{0-30}$ substituted or non-substituted alkylaminos and $C_{6-30}$ substituted or non-substituted arylaminos) such as amino, methylamino, dimethylamino, anilino, N-methyl-anilino and diphenylamino; acylaminos (preferably $C_{1-30}$ substituted or non-substituted alkylcarbonylaminos and $C_{6-30}$ substituted or non-substituted arylcarbonylaminos) such as formylamino, acetylamino, pivaloylamino, lauroylamino and benzoylamino; aminocarbonylaminos (preferably $C_{1-30}$ substituted or non-substituted aminocarbonylaminos) such as carbamoylamino, N,N-dimethylaminocarbonylamino, N,N-diethylamino carbonylamino and morpholino carbonylamino; alkoxycarbonylaminos (preferably $C_{2-30}$ substituted or non-substituted alkoxycarbonylaminos) such as methoxycarbonylamino, ethoxycarbonylamino, tert-butoxycarbonylamino, n-octadecyloxycarbonylamino and N-methyl-methoxy carbonylamino; aryloxycarbonylaminos (preferably $C_{7-30}$ substituted or non-substituted aryloxycarbonylaminos) such as phenoxycarbonylamino, p-chloro phenoxycarbonylamino and m-n-octyloxy phenoxy carbonylamino; sulfamoylaminos (preferably $C_{0-30}$ substituted or non-substituted sulfamoylaminos) such as sulfamoylamino, N,N-dimethylamino sulfonylamino and N-n-octylamino sulfonylamino; alkyl- and aryl-sulfonylaminos (preferably $C_{1-30}$ substituted or non-substituted alkyl-sulfonylaminos and $C_{6-30}$ substituted or non-substituted aryl-sulfonylaminos) such as methyl-sulfonylamino, butyl-sulfonylamino, phenyl-sulfonylamino, 2,3,5-trichlorophenyl-sulfonylamino and p-methylphenyl-sulfonylamino; mercapto; alkylthios (preferably substituted or non-substituted $C_{1-30}$ alkylthios such as methylthio, ethylthio and n-hexadecylthio; arylthios (preferably $C_{6-30}$ substituted or non-substituted arylthios) such as phenylthio, p-chlorophenylthio and m-methoxyphenylthio; heterocyclic-thios (preferably $C_{2-30}$ substituted or non-substituted heterocyclic-thios such as 2-benzothiazolyl thio and 1-phenyltetrazol-5-yl-thio; sulfamoyls (preferably $C_{0-30}$ substituted or non-substituted sulfamoyls) such as N-ethylsulfamoyl, N-(3-dodecyloxypropyl)sulfamoyl, N,N-dimethylsulfamoyl, N-acetylsulfamoyl, N-benzoylsulfamoyl, N—(N'-phenylcarbamoyl)sulfamoyl; sulfo; alkyl- and aryl-sulfinyls (preferably $C_{1-30}$ substituted or non-substituted alkyl- or $C_{6-30}$ substituted or non-substituted aryl-sulfinyls) such as methylsulfinyl, ethylsulfinyl, phenylsulfinyl and p-methylphenylsulfinyl; alkyl- and aryl-sulfonyls (preferably $C_{1-30}$ substituted or non-substituted alkyl-sulfonyls and $C_{6-30}$ substituted or non-substituted aryl-sulfonyls) such as methylsulfonyl, ethylsulfonyl, phenylsulfonyl and p-methylphenylsulfonyl; acyls (preferably $C_{2-30}$ substituted non-substituted alkylcarbonyls, and $C_{7-30}$ substituted or non-substituted arylcarbonyls) such as formyl, acetyl and pivaloyl benzoyl; aryloxycarbonyls (preferably $C_{7-30}$ substituted or non-substituted aryloxycarbonyls) such as phenoxycarbonyl, o-chlorophenoxycarbonyl, m-nitrophenoxycarbonyl and p-tert-butylphenoxycarbonyl; alkoxycarbonyls (preferably $C_{2-30}$ substituted or non-substituted alkoxycarbonyls) methoxycarbonyl, ethoxycarbonyl, tert-butoxycarbonyl and n-octadecyloxycarbonyl; carbamoyls (preferably $C_{1-30}$ substituted or non-substituted carbamoyls) such as carbamoyl, N-methylcarbamoyl, N,N-dimethylcarbamoyl, N,N-di-n-octylcarbamoyl and N-(methylsulfonyl)carbamoyl; aryl- and heterocyclic-azos (preferably $C_{6-30}$ substituted or non-substituted arylazos and $C_{3-30}$ substituted or non-substituted heterocyclicazos) such as phenylazo, p-chlorophenylazo, 5-ethylthio-1,3,4-thiadiazol-2-yl-azo; imidos such as N-succinimido and N-phthalimido; phosphinos (preferably $C_{2-30}$ substituted or non-substituted phosphinos) such as dimethyl phosphino, diphenyl phosphino and methylphenoxy phosphino; phosphinyls (preferably $C_{2-30}$ substituted or non-substituted phosphinyls) such as phosphinyl, dioctyloxy phosphinyl and diethoxy phosphinyl; phosphinyloxys (preferably $C_{2-30}$ substituted or non-substituted phosphinyloxys) such as diphenoxyphosphinyloxy and dioctyloxyphosphinyloxy; phosphinylaminos (preferably $C_{2-30}$ substituted or non-substituted phosphinylaminos) such as dimethoxy phosphinylamino and dimethylamino phosphinylamino; and silyls (preferably $C_{3-30}$ substituted or non-substituted silyls) such as trimethylsilyl, tert-butylmethylsilyl and phenyldimethylsilyl.

The substituents, which have at least one hydrogen atom, may be substituted by at least one substituent selected from these. Examples such substituent include alkylcarbonylaminosulfo, arylcarbonylaminosulfo, alkylsulfonylaminocarbonyl and arylsulfonylaminocarbonyl. More specifically, methylsulfonylaminocarbonyl, p-methylphenylsulfonylaminocarbonyl, acetylaminosulfonyl and benzoylaminosulfonyl are exemplified.

In formula (I), each of $R^1$ and $R^2$ may contain a polymerizable group. The polymerizable group in $R^1$ and $R^2$ are advantageous in producing the anisotropic material, such as optically anisotropic film, using the triazine derivative as a source material. Polymerization reaction of the polymerizable group is preferably addition polymerization (including ring-opening polymerization) or condensation polymerization. In other words, the polymerizable group is preferably a functional group capable of addition polymerization reaction or condensation polymerization reaction. Examples of the polymerizable group are shown below.

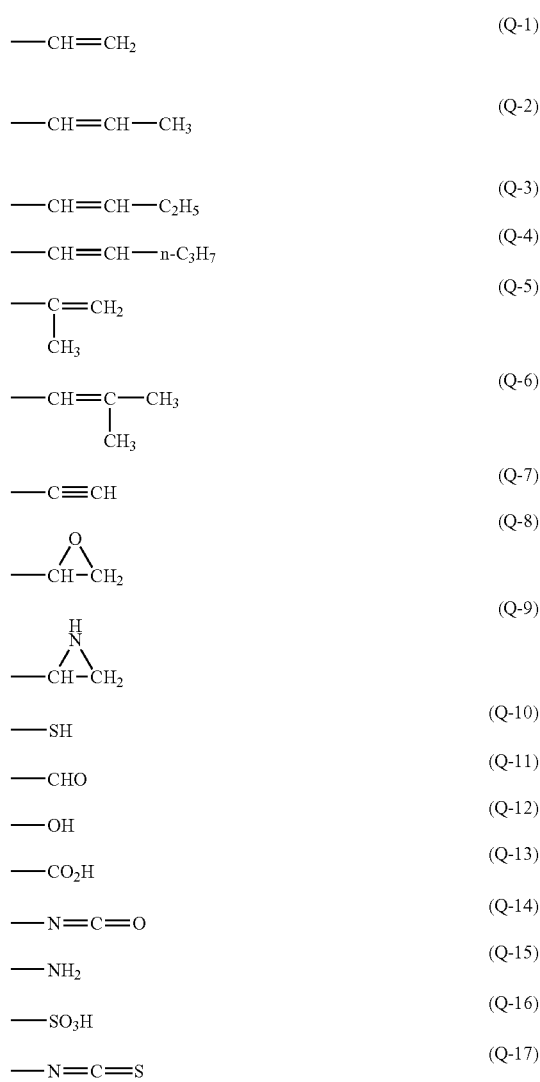

The polymerizable group is preferably an unsaturated polymerizable group (any one of Q-1 to Q-7), epoxy group (Q-8) or aziridinyl group (Q-9), more preferably an unsaturated polymerizable group, and still more preferably ethylenic unsaturated polymerizable groups (Q-1 to Q-6). More preferable examples of the ethylenic unsaturated polymerizable group include (Q-101) to (Q-106) below.

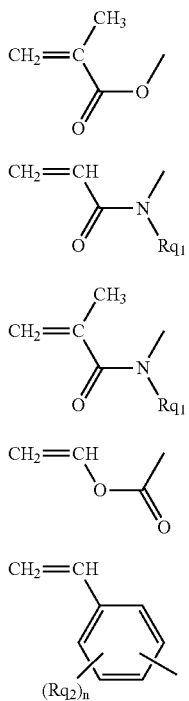

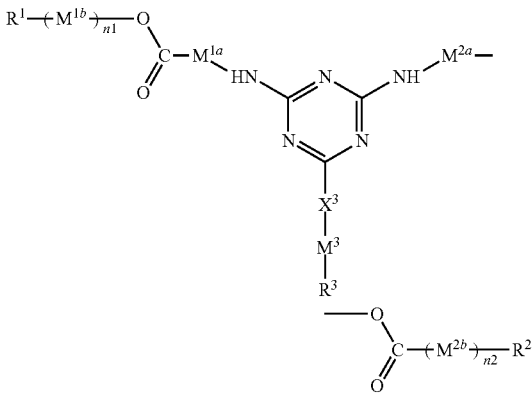

In the formula, $X^3$ represents a single bond, NH, S or O; $M^3$ is a divalent group containing one or more substituted or non-substituted aromatic rings; and $R^3$ represents a substituent. Each of $M^{1a}$, $M^{1b}$, $M^{2a}$, $M^{2b}$, n1, n2, $R^1$ and $R^2$ are synonymous with each of those in formula (I) in the above, and the same will apply to the preferable ranges.

In formula (II), $M^3$ may contain a substituted or non-substituted 1,4-phenylene group. More specifically, one preferable example of the triazine derivative represented by formula (I) is a triazine derivative represented by formula (III).

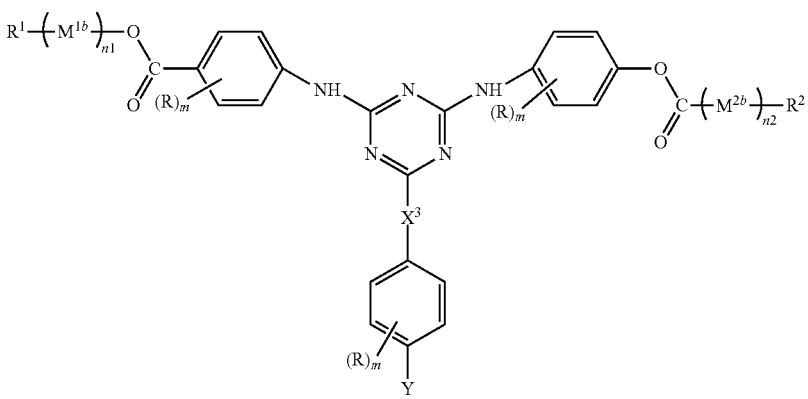

In the formulae, $Rq_1$ is a hydrogen atom, alkyl group or aryl group; $Rq_2$ is a substituent, and n is an integer from 0 to 4.

Specific examples of the alkyl group or aryl group are same as those exemplified for the group G of substituent described in the above. $Rq_1$ is preferably a hydrogen atom, alkyl group having 1 to 5 carbon atoms, or aryl group having 6 to 12 carbon atoms, more preferably a hydrogen atom, or alkyl group having 1 to 3 carbon atoms, and still more preferably a hydrogen atom or methyl group. As the substituent represented by $Rq_2$, any of those exemplified in the group G of substituent may preferably be adopted. In the formula, n is preferably an integer from 0 to 2, and more preferably 0 or 1.

In formula (I), X preferably contains one or more substituted or non-substituted aromatic ring, similarly to $M^{1a}$, $M^{1b}$, $M^{2a}$ and $M^{2b}$. More specifically, one preferable example of the triazine derivative represented by formula (I) is a triazine derivative represented by formula (II).

In the formula, each of $M^{1b}$, $M^{2b}$, $R^1$, $R^2$, n1 and n2 are synonymous with each of those in formula (I), and the same will apply to the preferable ranges. $X^3$ represents a single bond, NH, S or O, and preferably represents NH.

In the formula, each R represents a substituent; and each m represents an integer from 0 to 4. When there is a plurality of substituents R, they may be same with or different from each other. Examples of the substituent R include those in the group G of substituent. Among of those, F, Cl, Br, CN, $NO_2$, $CH_3$, $C_2H_5$, $OCH_3$, $OC_2H_5$, $COCH_3$, $COC_2H_5$, $CF_3$, $OCF_3$, $OCHF_2$, and $OC_2F_5$ are preferable; F, Br, Cl, CN, $CH_3$, $C_2H_5$, $OCH_3$, $COCH_3$ and $OCF_3$ are more preferable; and F, Br, $CH_3$, $OCH_3$ and $COCH_3$ are still more preferable.

In the formula, Y represents a substituent, and examples of the substituent Y may be exemplified by those in the group G of substituent. Y is preferably any of those represented by the formulae below.

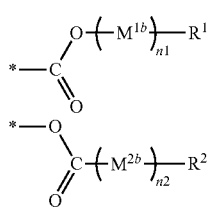

In the formulae, each of $M^{1b}$, $M^{2b}$, $R^1$, $R^2$, n1 and n2 are synonymous to each of those in formula (I), and the same will apply to preferable ranges.

The mark * indicates a binding site to benzene ring.

Specific examples of the compound include, but are not limited to, those shown below. First, specific examples of —NH-$M^{1a}$-C(=O)O-($M^{1b}$)-$R^1$, one of three substituents on the triazine ring shown in formula (I), will be shown.

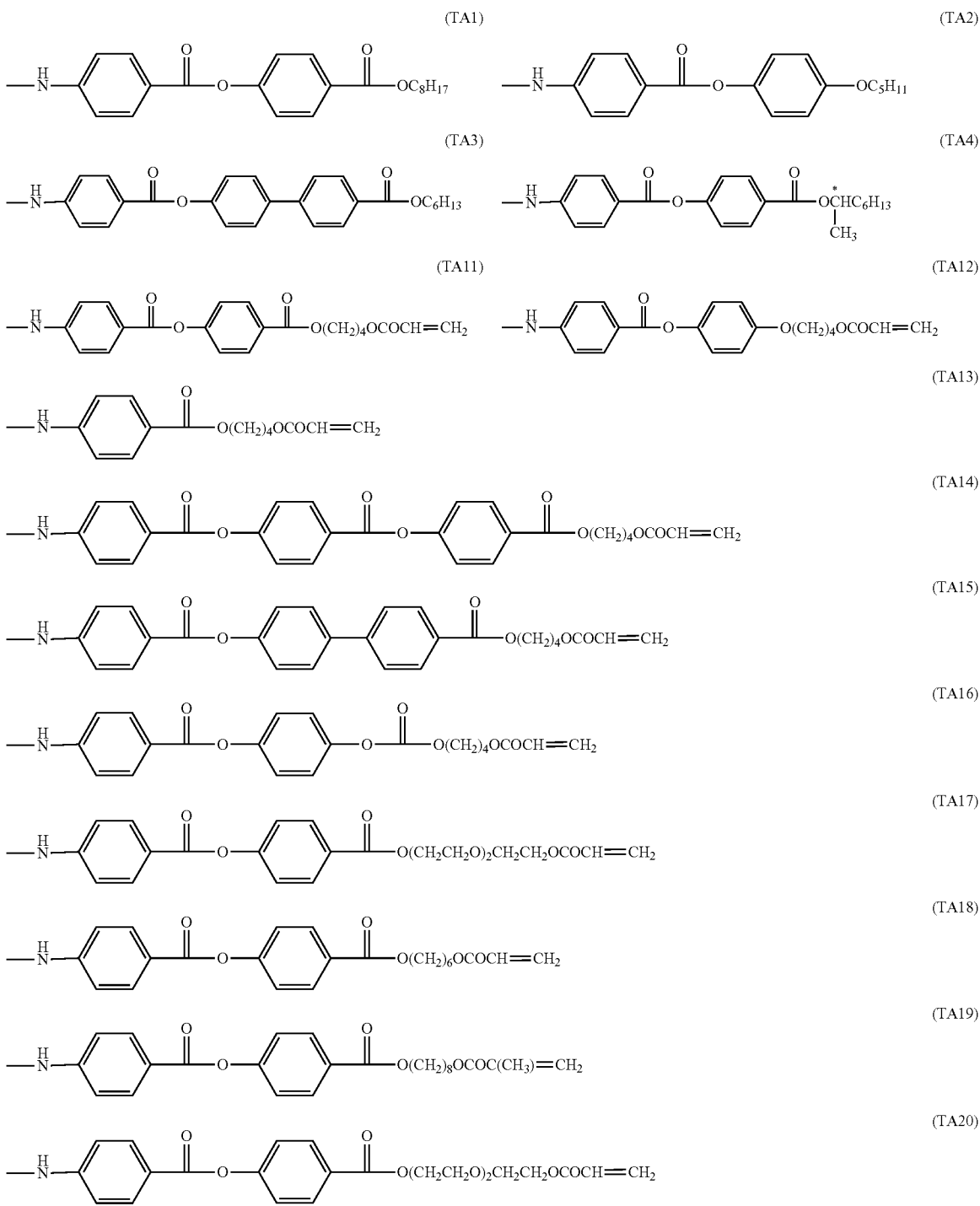

-continued
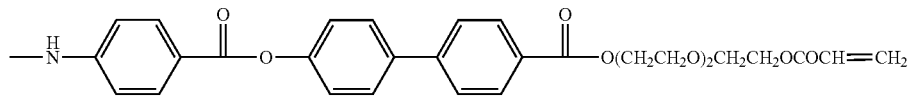
(TA21)
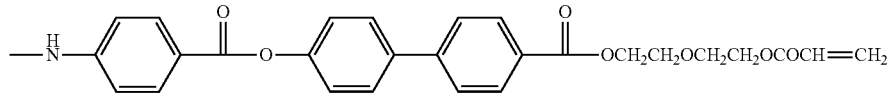
(TA22)
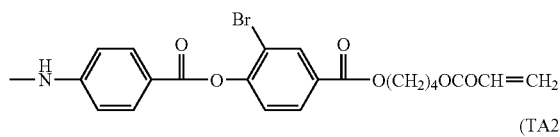
(TA23)
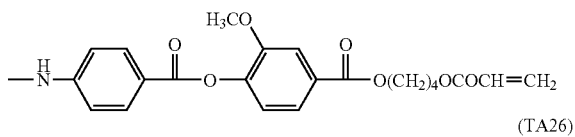
(TA24)
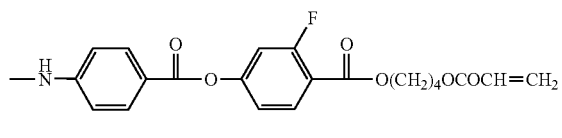
(TA25)
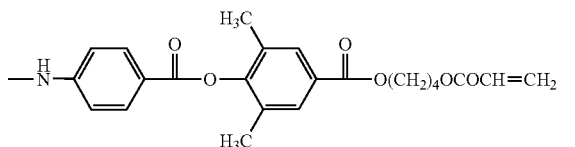
(TA26)
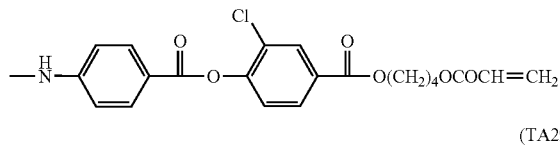
(TA27)
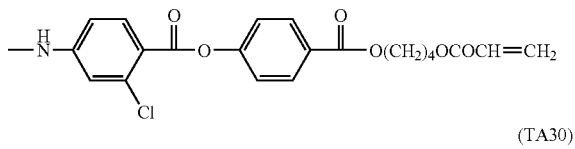
(TA28)
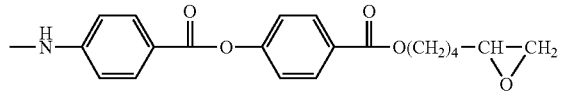
(TA29)
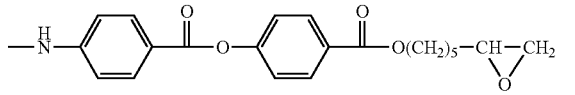
(TA30)
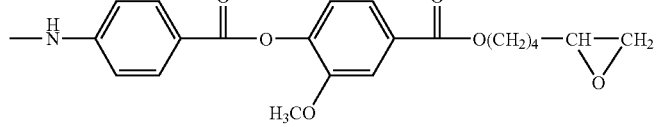
(TA31)
(TA32)
Next, specific examples of —NH-M$^{2a}$-OC(=O)-(M$^{2b}$)$_{n2}$-R$^2$, one of three substituents on the triazine ring shown in formula (I), will be shown.
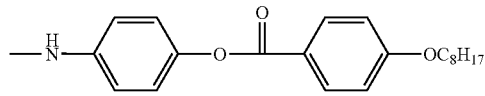
(TB1)
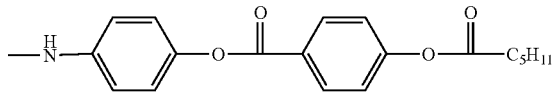
(TB2)
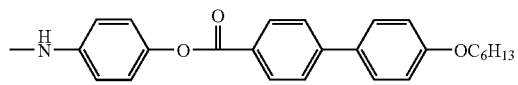
(TB3)
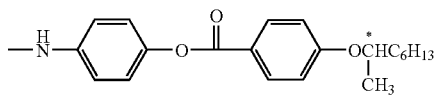
(TB4)
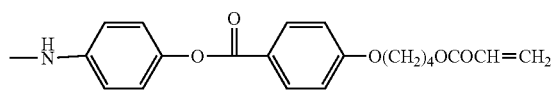
(TB11)
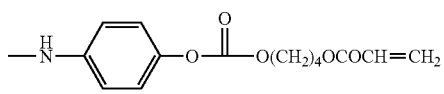
(TB12)

-continued (TB13) —NH—C₆H₄—O—C(O)—O(CH₂)₃OCOCH=CH₂

(TB14) —NH—C₆H₄—O—C(O)—C₆H₄—O—C(O)—C₆H₄—O(CH₂)₄OCOCH=CH₂

(TB15) —NH—C₆H₄—O—C(O)—C₆H₄—C₆H₄—O(CH₂)₄OCOCH=CH₂

(TB16) —NH—C₆H₄—O—C(O)—C₆H₄—OCO(CH₂)₅OCOCH=CH₂

(TB17) —NH—C₆H₄—O—C(O)—C₆H₄—O—C(O)—O(CH₂)₄OCOCH=CH₂

(TB18) —NH—C₆H₄—O—C(O)—C₆H₄—O(CH₂)₈OCOC(CH₃)=CH₂

(TB19) —NH—C₆H₄—O—C(O)—C₆H₄—OCH₂CH₂OCH₂CH₂OCOCH=CH₂

(TB20) —NH—C₆H₄—O—C(O)—C₆H₄—O(CH₂CH₂O)₂CH₂CH₂OCOCH=CH₂

(TB21) —NH—C₆H₄—O—C(O)—C₆H₄—C₆H₄—OCH₂CH₂OCH₂CH₂OCOCH=CH₂

(TB22) —NH—C₆H₄—O—C(O)—C₆H₄—C₆H₄—O(CH₂CH₂O)₂CH₂CH₂OCOCH=CH₂

(TB23) —NH—C₆H₄—O—C(O)—C₆H₃(Br)—O(CH₂)₄OCOCH=CH₂

(TB24) —NH—C₆H₄—O—C(O)—C₆H₃(OCH₃)—O(CH₂)₄OCOCH=CH₂

(TB25) —NH—C₆H₄—O—C(O)—C₆H₃(F)—O(CH₂)₄OCOCH=CH₂

(TB26) —NH—C₆H₄—O—C(O)—C₆H₂(CH₃)₂—O(CH₂)₄OCOCH=CH₂

(TB27) —NH—C₆H₄—O—C(O)—C₆H₃(Cl)—O(CH₂)₄OCOCH=CH₂

(TB28) —NH—C₆H₃(CH₃)—O—C(O)—C₆H₄—O(CH₂)₄OCOCH=CH₂

(TB29) —NH—C₆H₃(Cl)—O—C(O)—C₆H₄—O(CH₂)₄OCOCH=CH₂

(TB30) —NH—C₆H₄—O—C(O)—C₆H₄—O(CH₂)₅—CH(O)CH₂ (epoxide)

-continued

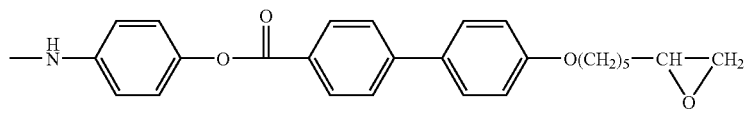
(TB31)

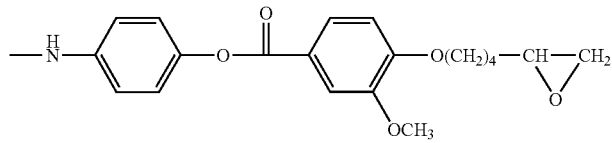
(TB32)

Next, specific examples of X, one of three substituents on the triazine ring shown in formula (I), will be shown. Besides them, also TA1 to TA32 and TB1 to TB32 shown in the above may be exemplified as the specific examples of X.

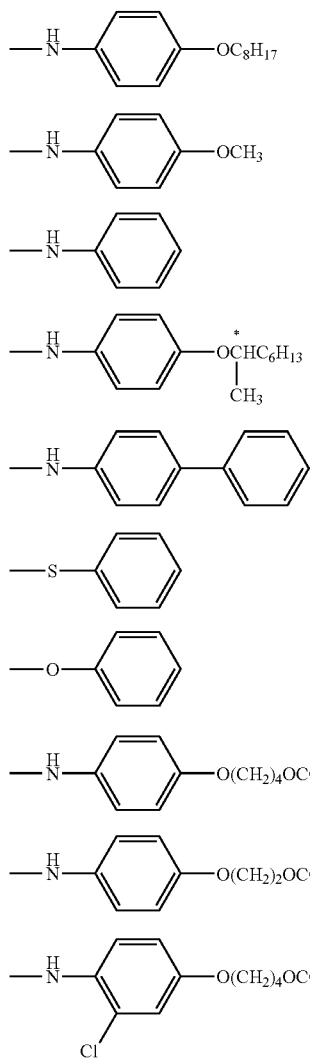

All triazine derivatives obtained by arbitrarily combining these substituents are preferable exemplary compounds.

Preferable examples of the compound are shown below. In the specific examples, $R^a$ corresponds to —NH-$M^{1a}$-C(=O)-O—$(M^{1b})_{n1}$-$R^1$, $R^b$ corresponds to —NH-$M^{2a}$-OC(=O)-$(M^{2b})_{n2}$-$R^2$ and $R^c$ corresponds to X in formula (I).

(TC1)

| Exemplary Compound No. | $R^a$ | $R^b$ | $R^c$ |
|---|---|---|---|
| (1) | TA1 | TB1 | TC2 |
| (2) | TA3 | TB3 | TC3 |
| (3) | TA4 | TB4 | TC3 |
| (4) | TA3 | TB3 | TC5 |
| (5) | TA4 | TB4 | TC5 |
| (6) | TA1 | TB1 | TA1 |
| (7) | TA1 | TB1 | TB1 |
| (8) | TA3 | TB3 | TA3 |
| (9) | TA4 | TB4 | TB4 |
| (10) | TA11 | TB11 | TC5 |
| (11) | TA11 | TB11 | TC11 |
| (12) | TA11 | TB11 | TA11 |
| (13) | TA11 | TB11 | TB11 |
| (14) | TA15 | TB11 | TB11 |
| (15) | TA15 | TB15 | TB15 |
| (16) | TA15 | TB20 | TB20 |
| (17) | TA15 | TB22 | TA15 |
| (18) | TA15 | TB22 | TB22 |
| (19) | TA15 | TB11 | TC2 |
| (20) | TA15 | TB20 | TC5 |
| (21) | TA21 | TB11 | TA21 |
| (22) | TA21 | TB15 | TB15 |
| (23) | TA21 | TB20 | TB20 |
| (24) | TA21 | TB22 | TB22 |
| (25) | TA21 | TB22 | TB21 |
| (26) | TA22 | TB11 | TA22 |
| (27) | TA22 | TB15 | TA22 |
| (28) | TA22 | TB20 | TB20 |
| (29) | TA22 | TB22 | TB22 |
| (30) | TA22 | TB22 | TC5 |

The triazine derivative of the present invention may be synthesized referring to various methods. Possible methods includes a method of allowing a side chain to react with a compound destined for a triazine ring kernel (for example, nucleophilic displacement reaction or coupling reaction of cyanuric chloride), and a method of obtaining a triazine ring compound by constructing a cyclic structure using a compound having side chains. Among others, a synthetic method based on reaction between cyanuric chloride and a compound having active hydrogen (amine and aniline derivatives) is preferable. Some of the exemplary synthesis will specifically be shown later in Examples.

Examples of the triazine derivative of the present invention include compounds showing liquid crystallinity. In the triazine derivative of the present invention, each of at least two substituents among the three substituents on the triazine ring have an ester bond therein, wherein the order of bonds of the ester bonds satisfies a specific relation. As shown below, the triazine derivative has dipole moment, induced in the direction indicated by the arrow, ascribable to a structural feature of the molecule. As a consequence, the triazine derivative is more likely to align in a highly ordered manner, and is capable of causing transition to a smectic phase at appropriate temperature. Such feature of readiness in alignment will not be inhibited, even if X in formula contains no ester bond, or even if the ester bonds contained therein are bound according to any order of bonds. Still even for the case where the triazine derivative of the present invention shows no liquid crystallinity, by using it in combination with a liquid crystalline compound, the triazine compound supposedly contributes to align molecules of the liquid crystalline compound in a highly ordered manner.

able group and liquid crystal compound include those described in Japanese translation of PCT international application No. 2000-514202 and JPA No. 2002-62427.

(Additive)

The liquid crystal composition may comprise one or more additives. Examples of the additive include alignment promoting agents, polymerization initiators, chain-transfer agents, plasticizers, surfactants and polymerizable monomers. These additives may be used for various purposes such as promotion of fixing the alignment or improvement in uniformity of the coated layer, in strength of the film or in alignment degree of the compound The additive preferably has a compatibility with the liquid crystalline molecules and has a property of not inhibiting the alignment thereof.

(Alignment-Promoting Agent)

The liquid crystal composition may comprise an additive capable of promoting the alignment of molecules of the triazine derivative of the invention or the liquid crystal com-

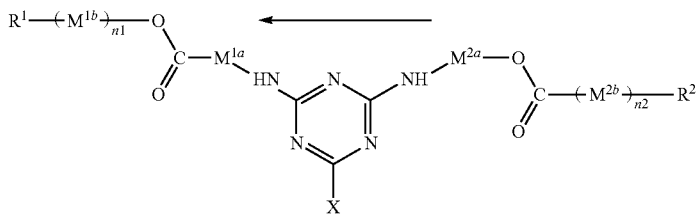

[Liquid Crystalline Composition]

The present invention relates also to a liquid crystalline composition comprising he triazine derivative of the present invention. The liquid crystalline composition may comprise only a single species of the triazine derivative of the present invention, or may comprise two or more species thereof. The liquid crystalline composition of the present invention is useful for producing anisotropic materials such as optically anisotropic film. In the embodiments wherein the triazine derivative has a polymerizable group, the composition is curable, and is useful for producing anisotropic film and so forth. The liquid crystalline composition more preferably shows the smectic phase, because the anisotropic material having more uniform characteristics may be produced.

(Liquid Crystal Compound)

The liquid crystal composition, if desired, may comprise one or more liquid crystal compound (preferably polymerizable liquid crystal compound) other than the compound of the invention. Another liquid crystal compound employable in the invention is not limited to any range, may be selected from various liquid crystal compounds capable of forming a nematic, smectic or cholesteric phase. Another liquid crystal compound is preferably selected from rod-like liquid crystal compounds, and, in particular, from azomethines, azoxys, cyanobiphenyls, cyanophenyl esters, benzoate esters, cyclohexane carboxylic acid phenyl esters, cyanophenyl cyclohexanes, cyano-substituted phenyl pyrimidines, alkoxy-substituted phenyl pyrimidines, phenyl dioxanes, tolans and alkenyl cyclohexyl benzonitriles.

As another liquid crystal compound, liquid crystal compound having a reactive moiety therein capable of polymerization or cross-linking reaction to be induced by active ray, electron ray, heat or the like. The number of the reactive moiety in a molecule is preferably from 1 to 6, and more preferably from 1 to 3. The moiety is preferably capable of polymerization, and preferably has a radical-polymerizable unsaturated group. In particular, examples of the polymerizpound to be used with the triazine derivative if desired. The amount of the alignment-promoting agent in the composition is preferably from 0.01 to 10 mass %, more preferably from 0.05 to 5 mass % and further more preferably from 0.05 to 4 mass % with respect to the amount of the liquid crystal compound. The alignment-promoting agent may achieve an excluded volume effect or an electrostatic effect at the air-interface or alignment-layer-interface thereby contributing to promoting of alignment of molecules of the liquid crystal compound. Examples of the agent employable include those described in JPA Nos. 2002-20363 and 2002-129162. And the techniques or the like described in JPA No. 2004-53981, [0072] to [0075], JPA No. 2004-4688, [0071] to [0078], and JPA No. 2004-139015, [0052] to [0054], [0065] to [0066] and [0092] to [0094] are applicable to the invention.

Examples of the agent capable of promoting vertical alignment of rod-like liquid crystal molecules include those described in JPA No. 2006-106662, [0078] to [0107], [0113] to [0118], [0162] to [0166] and [0189] to [0193].

Examples of the agent capable of promoting homogenous alignment of rod-like liquid crystal molecules include agents represented by formulae (I) to (III) described in JPA No. 2005-99248, [0058] to [0096] and the agents described in JPA No. 2006-126768, [0063] to [0069].

Single or plural of types of the additive may be employed in the invention.

(Polymerization Initiator)

Any heat-polymerization initiators and photo-polymerization initiators may be employed in the invention. Photo-polymerization initiators are preferred. Examples of the photo-polymerization initiator include α-carbonyl compounds (those described in U.S. Pat. Nos. 2,367,661 and 2,367,670), acyloin ethers (those described in U.S. Pat. No. 2,448,828), α-hydrocarbon-substituted aromatic acyloin compounds (those described in U.S. Pat. No. 2,722,512), polynuclear quinone compounds (those described in U.S. Pat. Nos. 3,046, 127 and 2,951,758), combinations of triarylimidazole dimer and p-aminophenyl ketone (those described in U.S. Pat. No. 3,549,367), acrydine and phenazine compounds (those described in JPA No. S60-105667 and U.S. Pat. No. 4,239, 850), and oxadiazole compounds (those described in U.S. Pat. No. 4,212,970).

The amount of the polymerization initiator in the composition is preferably from 0.01 to 20 mass %, and more preferably from 0.5 to 10 mass % with respect to the total mass of the composition (the total mass of the solid content when the composition is a coating fluid).

(Chain-Transfer Agent)

The liquid crystal composition of the invention may comprise single or plural types of chain-transfer agent. The amount of the agent in the composition is preferably from 0.01 to 10 mass %, more preferably 0.05 to 5 mass %, and further more preferably from 0.05 to 4 mass % with respect to the amount of the liquid crystal compound. Various types of, the agent may be used, and preferred examples of the agent include compounds having a mercapto group such as thiol compounds (e.g., dodecyl mercaptan, octyl mercaptan, trimethylolpropane tris(3-mercapto propionate), and pentaerythritol tetrakis(3-mercapto propionate) and disulfide compounds (e.g., dipehnyl disulfide). The agent may be required to have a compatibility with the liquid crystalline molecules, and in terms of its compatibility, thiol compounds are preferred. Examples of the thiol compound having a liquid-crystallinity include the compounds described in U.S. Pat. No. 6,096,241.

(Polymerizable Monomer)

Examples of the polymerizable monomer employable in the invention include compounds capable of radical- or cation-polymerization. Preferred are multifunctional radical-polymerization monomers, and more preferred are multifunctional radical-polymerization monomers capable of co-polymerization with the liquid crystal compound.

Examples of the employable monomer include the compounds describe in JPA No. 2002-296423, [0018] to [0020]. Examples of bivalent (meth)acrylate include ethylene glycol (meth)acrylate, 1,6-hexane diol (meth)acrylate, polypropylene glycol (meth)acrylate, and tetra ethylene glycol (meth) acrylate. Examples of trivalent or more multivalent (meth) acrylate include trimethylol propane tri(meth)acrylate, pentaerythritol tri(meth)acrylate, tri((meth)acryloyloxy ethyl)phosphate, pentaerythritol tetra(meth)acrylate, di-pentaerythritol penta (meth)acrylate, di-pentaerythritol hexa (meth)acrylate, poly (meth)acrylate of polyether based polyol, poly(meth)acrylate of polyester based polyol, and poly(meth)acrylate of polyurethane based polyol.

Such multivalent monomer may be used singularly or in combination with other monomers. Any combination of monomers may be advantageous in terms of viscosity and adjustment of strength. The amount of the monomer in the composition is preferably from 1 to 50 mass % and more preferably from 1 to 30 mass % with respect to the total mass of the liquid crystal compound.

(Surfactant)

Any surfactant may be employed in the invention, and fluorochemical surfactants are preferred. Examples of the surfactant include the compounds described in JPA No. 2001-330725, [0028] to [0056].

(Polymer Additive)

The liquid crystal composition may comprise a polymer additive. The polymer additive may be used not only to promote alignment of liquid crystal molecules but also to adjust the composition's surface tension and viscosity to the preferred range; and any polymers, having such properties, soluble in the composition can be used.

The polymer additive, which is used for the purpose of promoting alignment of liquid crystal molecules, preferably has a moiety capable of achieving an excluded volume effect or an electrostatic effect at the air-interface or the alignment-layer interface to thereby promote alignment of liquid crystal molecules. The polymer additive to be used for the purpose of achieving the effect at the air-interface is preferably selected from the polymers comprising a unit derived from a fluoroaliphatic-group containing monomer and a unit capable of promoting the alignment.

The polymer additive to be used for the purpose of adjusting the composition's viscosity to the preferred range is preferably selected from the polymers capable of increasing the viscosity of a solution thereof; and examples of such a polymer include cellulose esters. Preferred examples of cellulose ester include those described in JPA No. 2000-155216, [0178].

The polymer additive to be used for the purpose of adjusting the composition's surface tension to the preferred range is preferably selected from the polymers capable of decreasing the surface tension of a solution thereof; and examples of such a polymer include polymers having fluorine atom(s) therein. Any known fluorine-containing polymers and fluorochemical surfactants can be used. Among these, polymers comprising a unit derived from a fluoroaliphatic-group containing monomer are preferred.

The weight-average molecular weight (MW) of the polymer additive is preferably from 1000 to 1000000, more preferably from 2000 to 200000, and further more preferably from 3000 to 100000.

The amount of the polymer additive in the composition is preferably from 0.01 to 50 mass %, more preferably from 0.05 to 20 mass % and further more preferably from 0.1 to 10 mass % with respect to the amount of the liquid crystal compound for avoiding the inhibition of the alignment of liquid crystal molecules.

(Coating Liquid)

The liquid crystal composition may be prepared as a coating liquid.

Organic solvents are preferably used for preparing the coating fluid. Examples of the organic solvent include amides such as N,N-dimethyl formamide, sulfoxides such as dimethyl sulfoxide, heterocyclic compounds such as pyridine, hydrocarbons such as benzene and hexane, alkyl halides such as chloroform and dichloromethane, esters such as methyl acetate and butyl acetate, ketones such as acetone and methyl ethyl ketone, ethers such as tetrahydrofuran and 1,2-dimethoxy ethane. Among those, alkyl halides, esters and ketones are preferable; and esters and ketones are especially preferable. Two or more types of organic solvents may be used.

[Anisotropic Material]

The present invention also relates to an anisotropic material made of liquid crystalline composition of the present invention. The anisotropic material of the present invention is useful typically as an optical compensation element of liquid crystal display devices. In particular, an anisotropic material, formed by using a liquid crystalline composition capable of showing the smectic phase, and by fixing the smectic phase has more uniform optical characteristics.

An optically anisotropic film, as one embodiment of the anisotropic material of the present invention, will be detailed below.

(Method of Producing Optically Anisotropic Film)

The optically anisotropic film may be produced typically by preparing the liquid crystalline composition of the present invention as a coating liquid, applying the coating liquid onto the surface (for example, surface of an alignment film), drying the coated film so as to attain a desired state of alignment, and then curing it.

The coating liquid may be applied according to any of known methods (for example, extrusion coating, direct gravure coating, reverse gravure coating, and die coating).

After the applying step, the coated film is dried so as to remove a solvent in the coating liquid, and so as to attain a desired state of alignment. The drying may be carried out under heating, if desired. The triazine derivative of the present invention, characterized by its tendency of alignment in a highly ordered manner, and readiness of expressing the smectic phase, may be transferred into the smectic phase at appropriate temperatures. Temperature for drying is preferably 20 to 200° C., and more preferably 40 to 180° C. However, the temperature range is not limited thereto. In particular, the smectic phase may be fixed in a more highly ordered manner, by, after the applying step, keeping the coated film once in the nematic phase or isotropic phase, then cooling the coated film so as to turn it into the smectic phase. When the coated film is kept in the menatic phase or isotropic phase, the temperature is set higher than the transition temperature $T_s°$ C. to the smectic phase, which is preferably $T_s+0.1°$ C. or above, more preferably $T_s+1°$ C. or above, and still more preferably $T_s+5°$ C. to $T_s+20°$ C. The period for keeping the nematic phase or isotropic phase under heating is preferably 10 seconds or longer, more preferably 20 seconds or longer, and still more preferably 30 seconds or longer but 3 minutes or shorter.

The optically anisotropic film is formed by aligning molecules of the liquid crystal compound in a desired alignment state (preferably in the smectic phase), and then fixing the alignment state. The fixation may be carried out by a polymerization reaction of polymerizable compounds. The polymerizable reaction carried out for the fixation preferably makes use of photo-polymerization reaction using a photo-polymerization initiator. Irradiation of light for polymerizing the liquid crystalline molecules preferably adopts ultraviolet radiation. Irradiation energy is preferably 20 mJ/cm$^2$ to 50 J/cm$^2$, and more preferably 100 to 800 mJ/cm$^2$. For the purpose of enhancing the photo-polymerization reaction, light may be irradiated under heating conditions.

Thickness of the optically anisotropic film is preferably 0.1 to 10 μm, more preferably 0.2 to 5 μm, and still more preferably 0.5 to 5 μm.

(Alignment Layer)

An alignment layer may be used for preparing the optically anisotropic layer. The alignment layer may have a function of controlling the orientation direction of liquid crystal molecules. The alignment layer may also be used for improving uniformity of alignment or adhesion between the optically anisotropic layer and a polymer film used for supporting the layer. After fixing the alignment state, the alignment layer may be removed since it finished its function. That is, after fixing the alignment state, the optically anisotropic layer may be transferred from on the surface of the alignment layer to on another surface of a support, polarizer or the like.

There have been provided alignment layers formed of various materials by various methods such as subjecting a film made of an organic compound (preferably a polymer) to a rubbing treatment, obliquely depositing an inorganic compound, forming a layer having microgrooves, or accumulating an organic compound (e.g., ω-trichosanic acid, dioctadecylmethylammonium chloride, methyl stearate) by Langmuir-Blodgett method (LB film). Alignment layers having an alignment effect under an electric or magnetic field or irradiation are also known. Among these, alignment layers prepared by subjecting a film of a polymer to a rubbing treatment are preferred.

Examples of the polymer used for preparing an alignment layer include methacrylate copolymers described in the column [0022] in JPA No. hei 8-338913, styrene copolymers, polyolefins, polyvinyl alcohols, modified polyvinyl alcohols, poly(N-methylol acrylamide), polyesters, polyimides, vinyl acetate copolymers, carboxymethylcelluloses and polycarbonates. Silane coupling agents are also used as a polymer.

Water-solbule polymers such as poly(N-methylol acrylamide), carboxymethylcelluloses, gelatins, polyvinyl alcohols or modified polyvinyl alcohols are preferred; gelatins, polyvinyl alcohols and modified polyvinyl alcohols are more preferred; and polyvinyl alcohols and modified polyvinyl alcohols are much more preferred. Using plural polyvinyl alcohols or modified polyvinyl alcohols, they have a different polymerization degree each other, is especially preferred.

The saponification degree of the polyvinyl alcohol is desirably from 70 to 100%, and more desirably from 80 to 100%. The polymerization degree of the polyvinyl alcohol is desirably from 100 to 5000.

Examples of polyimide, which can be used from preparing the alignment layer, include "SE-150", "SE-2170", "SE-130" and "SE-3140" manufactured by NISSAN CHEMICAL INDUSTRIES LCD.

The polymer may have a side chain capable of aligning liquid crystalline molecules. In usual, such a side chain having a function capable of aligning liquid-crystalline molecules may have a hydrophobic group as a function group. The types of the function group may be decided depending on various factors such as types of the liquid-crystalline compounds or desired alignment state. For example, the modified group can be introduced into the polyvinyl alcohol by copolymerization modification, chain-transfer modification or bloc-polymerization modification. Examples of the modified group include hydrophilic groups such as a carboxylic acid group, a sulfonic acid group, a phosphoric acid group, an amino group, an ammonium group, an amide group or a thiol group; $C_{10-100}$ hydrocarbon groups; hydrocarbon groups substituted with fluorine atoms; thioether groups, polymerizable groups such as an unsaturated polymerizable group, an epoxy group or an aziridile group; and alkoxysilyl groups such as tri-, di- or mono-alkoxysilyl group. Specific examples of such modified polyvinyl alcohols include those described in the columns [0022] to [0145] in JPA No. 2000-155216 and those described in the columns [0018] to [0022] in JPA No. 2002-62426.

It is possible to copolymerize a polymer in an alignment layer and a multi-functional monomer in an optically anisotropic layer, when the polymer in the alignment layer has a main chain bonding to side chains containing a crosslinkable functional group, or the polymer in the alignment layer has side chain being capable of aligning liquid-crystalline molecules and containing a crosslinkable functional group. In such case, not only between the multi-functional monomers but also between the polymers in the alignment layer and the multi-functional monomers and the polymers in the alignment layer, the covalent bondings are formed and the bonding strengths are improved. Thus, in such case, the strength of the optically anisotropic layer can be remarkably improved.

The polymer in the alignment layer desirably has crosslinkable functional group containing a polymerizable group. Specific examples include those described in the columns of [0080] to [0100] in JPA No. 2000-155216.

The polymer in the alignment layer may be crosslinked by a crosslinkable agent.

Examples of the crosslinkable agent include aldehydes, N-methylol compounds, dioxane derivatives, compounds to act when being activated their carboxyl groups, active vinyl compounds, active halogen compounds, isoxazoles and dialdehyde starches. Single or plural type of crosslinkable agents may be used. Specific examples of the crosslinkable agent include the compounds described in the columns [0023] to [0024] in JPA No. 2002-62426. Aldehydes having a high reaction-activity are preferred, and glutaraldehydes are more preferred.

The amount of the crosslinkable agent is desirable from 0.1 to 20 mass %, and more desirably 0.5 to 15 mass %, with respect to the mass of the polymer. The residual amount of the unreacted crosslinkable-agent in the alignment layer is desirably not greater than 1.0 mass %, and more desirably not greater than 0.5 mass %. When the residual amount falls within the range, the alignment layer has a sufficient durability, and even if the alignment layer is used in a liquid-crystal display for a long time, or is left under a high temperature and humidity atmosphere for a long time, no reticulation is appeared in the alignment layer.

The alignment layer may be prepared by applying a coating fluid, containing the above polymer, and, if necessary, the corsslinkable agent, to a surface of a support, drying under heating (crosslinking), and performing a rubbing treatment. The crosslinking reaction may be carried out any time after applying the coating fluid to a surface. When a hydrophilic polymer such as polyvinyl alcohol is used for preparation of an alignment layer, the coating fluid is desirably prepared using a mixed solvent of an organic solvent such as methanol, exhibiting a deforming function, and water. The weight ratio of water to methanol is desirably from 0/100 to 99/1, and more desirably from 0/100 to 91/9. Using such a mixed solvent can prevent bubbles from generating, and can remarkably reduce defects in the surface of the alignment layer and the optically anisotropic layer.

The coating liquid may be applied by any known method such as a spin-coating method, a dip coating method, a curtain coating method, extrusion coating method, rod coating method, or roll coating method. The rod coating method is especially preferred. The thickness of the alignment layer after being dried is desirably from 0.1 to 10 micrometers. Drying may be carried out at 20 to 110° C. In order to form sufficient crosslinking, drying is desirably carried out at 60 to 100° C., and more desirably at 80 to 100° C. The drying may be continued for 1 minute to 36 hours, and desirably for 1 minute to 30 minutes. The pH is desirably set in a proper range for a crosslinkable agent to be used, and when glutaraldehyde is used, the pH is desirably set in a range from 4.5 to 5.5, and more desirably 4.8 to 5.2.

The alignment layer may be formed on a surface of a support such as a polymer film or a surface of an under coating layer which is optionally formed on a support. The alignment layer can be obtained by applying a rubbing treatment to the surface of the polymer layer after crosslinking the polymer layer.

The rubbing treatment may be carried out according to any known treatment used in a liquid-crystal alignment step of LCD. For example, the rubbing treatment may be carried out by rubbing the surface of a polymer layer with a paper, a gauze, a felt, a rubber, a nylon fiber, polyester fiber or the like in a direction. Usually, the rubbing treatment may be carried out by rubbing a polymer layer with a fabric in which fibers having a uniform length and line thickness are implanted averagely at several times.

(Substrate for Supporting Optically Anisotropic Layer)

The optically anisotropic film may be formed on a substrate. The substrate is preferably transparent, and, in particular, preferably has a light transmission of not less than 80%.

The substrate may be selected from polymer films. Examples of materials for the substrate, however not limited to them, include cellulose esters, polycarbonates, polysulfones, polyethersulfones, polyacrylates and polymethacrylates. Cellulose ester films are preferable; cellulose acetate films are more preferable; and cellulose triacetate films are much more preferable. The polymer films prepared according to a solvent casting method are preferable. The thickness of the substrate is preferably from 20 to 500 μm, and more preferably from 40 to 200 μm. For improving adhesiveness between the substrate and a layer such as an adhesive layer, alignment layer and optically anisotropic layer disposed thereon, any surface treatment (e.g. glow discharge treatment, corona discharge treatment, UV irradiation treatment, flame treatment and saponification treatment) may be applied to the surface of the substrate. An adhesion layer (undercoating layer) may be formed on the substrate. In terms of slipping in a transporting step or preventing surfaces from sticking each other in a rolling-up state, a polymer layer comprising inorganic particles, having a mean particle size of 10 to 100 nm, in a solid-content amount of 5% to 40%, may be formed on a side of the (long) substrate according to a coating method or co-flow casting method.

The anisotropic material of the present invention is not limited to the above-described embodiment of optically anisotropic film, whereas the embodiment may also be anisotropic electro-conductive material, anisotropic heat-conductive material, and so forth.

[Applications]

Applications of the optically anisotropic film of the present invention will be explained.

The optically anisotropic film of the present invention may be used for various applications. For example, it is useful as an optical compensation film used for optical compensation of liquid crystal cells, or as a protective film for polarizing plates.

[Protective Film for Polarizing Plate]

Film obtained by forming the optically anisotropic film of the present invention onto a polymer film, more preferably a cellulose film, is useful as a protective film for polarizing plates. It is preferable to bond the surface of the polymer film such as cellulose acylate film to the surface of the polarizing film.

For the case of using it as the protective film for polarizing plate, methods of producing the polarizing plate are not specifically limited, and such a polarizing plate can be produced according to any general method. There is known a method of treating the back surface of thus-obtained films with alkali, and then bonding the films onto both surfaces of a polarizing film, manufactured by immersing a polyvinyl alcohol film into an iodine solution and then by stretching it, using an aqueous solution of completely saponified polyvinyl alcohol. In place of the alkali treatment, simple adhesion such as described in JPA Nos. H6-94915 and H6-118232 may be adoptable.

Adhesive used for bonding thus-treated surface of the protective film and the polarizing film may be exemplified typically by polyvinyl alcohol-base adhesives such as polyvinyl alcohol and polyvinyl butyral, and vinyl-base latex such as butyl acrylate.

The polarizing plate is composed of the polarizing film and the protective films protecting both surfaces thereof, wherein another possible configuration is such as bonding a protective film on one surface of the polarizing plate, and bonding a separation film on the opposite surface. The protective film and the separation film are used for the purpose of protecting the polarizing film in the process of shipping, inspection of products, and so forth. The protective film is bonded for the purpose of protecting the surface of the polarizing film, and is used on the surface of the polarizing film opposite to the surface to be bonded to the liquid crystal cell. On the other hand, the separate film is used for the purpose of covering an adhesive layer used for bonding it to the liquid crystal cell, and is used on the side of the surface of the polarizing plate to be bonded to the liquid crystal cell.

Liquid crystal display device generally has two polarizing plates and substrates placed therebetween containing a liquid crystal, wherein the protective film for the polarizing plate adopting the above-described film may ensure excellent display performance irrespective of position of placement.

[Optical Compensation Film]

The optically anisotropic film of the present invention is particularly effective when it is used as an optical compensation film of liquid crystal display devices. The optical compensation film herein refers to an optical material used in liquid crystal display devices, aimed at compensating retardation, and is synonymous with retardation plate, optical compensation sheet and so forth. The optical compensation film shows birefringence, and is used typically for eliminating coloration of displayed image on the liquid crystal display devices, and for improving the viewing angle characteristics.

(Configuration of General Liquid Crystal Display Device)

For the case where the optically anisotropic film of the present invention is used as an optical compensation film, the slow axis of the optically anisotropic film may be arranged in any angular relation with respect to the transmission axis of the polarizing plate.

The liquid crystal display device is configured as having a liquid crystal cell comprising two electrode substrates and a liquid crystal held therebetween, the polarizing plates arranged on both sides of the cell, and at least one optical compensation film placed between the liquid crystal cell and the polarizing film.

A liquid crystal layer of the liquid crystal cell may be formed generally by encapsulating a liquid crystal into a space formed by placing spacers between two substrates. Transparent electrode layers are formed as transparent films containing an electro-conductive substance. The liquid crystal cell may be further provided with a gas barrier layer, hard coat layer, or under coat layer (used for adhesion of the transparent electrode layer). These layers are generally provided on the surface of the substrates. Each of the substrates of the liquid crystal cell preferably has a thickness of 50 μm to 2 mm.

[Liquid Crystal Display Device]

The present invention also relates to a liquid crystal display device comprising the optically anisotropic film of the present invention. One or more optically anisotropic films of the present invention are used for liquid crystal display devices of various display modes, for the purpose of canceling coloration of images, and widening the viewing angle. The liquid crystal display device of the present invention may employ a transmission mode or a reflection mode. Also there are no limitation in the display modes, so that the present invention may be adoptable to any display modes of TN (twisted nematic), IPS (in-plane switching), OCB (optically compensatory bend), VA (vertically aligned), ECB (electrically controlled birefringence) and so forth.

(TN-Type Liquid Crystal Display Device)

The optically anisotropic film of the present invention may be used also as an optical compensation sheet of TN-type liquid crystal display devices having TN-mode liquid crystal cells. The TN-mode liquid crystal cells and the TN-type liquid crystal display devices have been well known. The optical compensation sheet used for the TN-type liquid crystal display devices are described in JPA Nos. H3-9325, H6-148429, HB-50206, and H9-26572. Descriptions may be found also in literatures by Mori et al. (Jpn. J. Appl. Phys., Vol. 36 (1997), p. 143, and Jpn. J. Appl. Phys., Vol. 36 (1997), p. 1068).

(STN-Type Liquid Crystal Display Device)

The optically anisotropic film of the present invention may be used also as an optical compensation sheet of STN-type liquid crystal display devices having STN-mode liquid crystal cells. Generally in the STN-type liquid crystal display devices, rod-like liquid crystalline molecules in the liquid crystal cell are twisted by an angle ranging from 90 to 360°, and product ($\Delta$nd) of refractive index anisotropy ($\Delta$n) of the rod-like liquid crystalline molecules and cell gap (d) falls in the range from 300 to 1500 nm. The optical compensation sheet used for the STN-type liquid crystal display devices are described in JPA No. 2000-105316.

(VA-Type Liquid Crystal Display Device)

The optically anisotropic film of the present invention is particularly useful as an optical compensation sheet for VA-type liquid crystal display devices having VA-mode liquid crystal cells. The optical compensation sheet used for the VA-type liquid crystal display devices preferably has Re value adjusted to 0 to 150 nm, and Rth value adjusted to 70 to 400 nm. For the case where two optically anisotropic films are used for the VA-type liquid crystal display device, Rth values of the films are preferably adjusted to 70 to 250 nm. For the case where a single optically anisotropic film is used for the VA-type liquid crystal display device, Rth value of the film preferably falls in the range from 150 to 400 nm. The VA-type liquid crystal display device may have a multi-domain system such as described, for example, in JPA No. H10-123576.

(IPS-Type Liquid Crystal Display Device and ECB-Type Liquid Crystal Display Device)

The optically anisotropic film of the present invention is useful also as an optical compensation sheet for IPS-type liquid crystal display devices and ECB-type liquid crystal display devices respectively employing IPS-mode and ECB-mode liquid crystal cells. These modes are characterized by embodiments in which liquid crystal materials align nearly parallel in the black state, wherein the black state is obtained by aligning liquid crystal molecules to align in the cell horizontally with respect to the surface of the substrates under absence of applied voltage. In these embodiments, the polarizing plate making use of the above-described optically anisotropic film contributes to improvement in hue, widening the viewing angle, and improvement in contrast. In these embodiments, at least one of the polarizing plates placed on the upper and lower sides of the liquid crystal cell preferably has the protective film, making use of the optically anisotropic film, placed between the liquid crystal cell and the polarizing plate (protective film on the cell side). It is still more preferable to dispose the optically anisotropic layer between the protective film of the polarizing plate and the liquid crystal cell, and to adjust retardation value of thus-disposed optically anisotropic layer twice or less as large as $\Delta$n·d value of the liquid crystal layer.

(OCB-Type Liquid Crystal Display Device and HAN-Type Liquid Crystal Display Device)

The optically anisotropic film of the present invention is useful also as an optical compensation sheet for OCB-type liquid crystal display devices having OCB-mode liquid crystal cells, or for HAN-type liquid crystal display devices having HAN-mode liquid crystal cells. The optical compensation sheet used for the OCB-type liquid crystal display devices or the HAN-type liquid crystal display devices preferably has directions in which absolute value of retardation value is minimized neither in the in-plane direction nor normal line direction of the optical compensation sheet. Also optical properties of the optical compensation sheet used for the OCB-type liquid crystal display devices or the HAN-type liquid crystal display devices are determined by optical properties of the optically anisotropic layer, optical properties of the substrate supporting the layer, and the arrangement of the optically anisotropic layer and the support. The optical compensation sheet used for the OCB-type liquid crystal display devices or the HAN-type liquid crystal display devices may be produced according to the method described in JPA No. H9-197397, and the literature by Mori et al., (Jpn. J. Appl. Phys., Vol. 38 (1999), p. 2837).

(Reflection-Type Liquid Crystal Display Device)

The optically anisotropic film of the present invention is useful also as an optical compensation sheet for reflection-type liquid crystal display devices of the TN-type, STN-type, HAN-type and GH (guest-host)-type. These display modes have been well known. The TN-type, reflection-type liquid crystal display device may be produced according to a method described in JPA No. H10-123478, Pamphlet of International Patent Publication WO98/48320, and Examined Japanese Patent Publication, JPB, No. 3022477. The optical compensation sheet used for the reflection-type liquid crystal display devices may be produced according to a method described in Pamphlet of International Patent WO00/65384.

(Other Liquid Crystal Display Devices)

The optically anisotropic film of the present invention is useful also as an optical compensation sheet for ASM-type liquid crystal display devices having ASM (axially symmetric aligned microcell)-mode liquid crystal cells. The ASM-mode liquid crystal cells are characterized in that thickness of the cells is maintained by position-adjustable resin spacers. Other properties are same as those of the TN-mode liquid crystal cells. The ASM-mode liquid crystal cells and the ASM-type liquid crystal display devices may be produced according to a method described in a literature by Kume et al., (SID 98 Digest 1089(1998)).

(Hard Coat Film, Anti-Glare Film, Anti-Reflective Film)

The optically anisotropic film of the present invention may preferably be used for hard coat film, anti-glare film, and anti-reflective film. Any one of, or all of the hard coat layer, anti-glare layer, and anti-reflective layer may be provided to one surface or both surfaces of the above-described film, for the purpose of improving recognizability of flat panel displays such as LCD, PDP, CRT, and EL display. Preferable embodiments as the anti-glare film and anti-reflective film are detailed in JIII Journal of Technical Disclosure (No. 2001-1745, p. 54-57, issued on Mar. 15, 2001, JIII), wherein the above-described film may preferably be adoptable.

The triazine derivative, liquid crystal composition and the optically anisotropic film formed using the composition may be used for producing not only display materials but also opto-electronics materials, photonics materials and so forth, without being limited to the above-described applications.

EXAMPLES

Paragraphs below will further specifically describe features of the present invention, referring to Examples and Comparative Examples. Any materials, amount of use, ratio, details of processing, procedures of processing and so forth shown in Examples may appropriately be modified without departing from the spirit of the present invention. Therefore, it is to be understood that the scope of the present invention should not be interpreted in a limited manner based on the specific examples shown below.

Example 1

[Exemplary Synthesis: Synthesis of Exemplary Compound (14)]

An Exemplary Compound (14) was synthesized according to the following scheme. The individual steps were proceeded according to publicly-known methods of synthesis. Structures of the products were identified based on various spectral data.

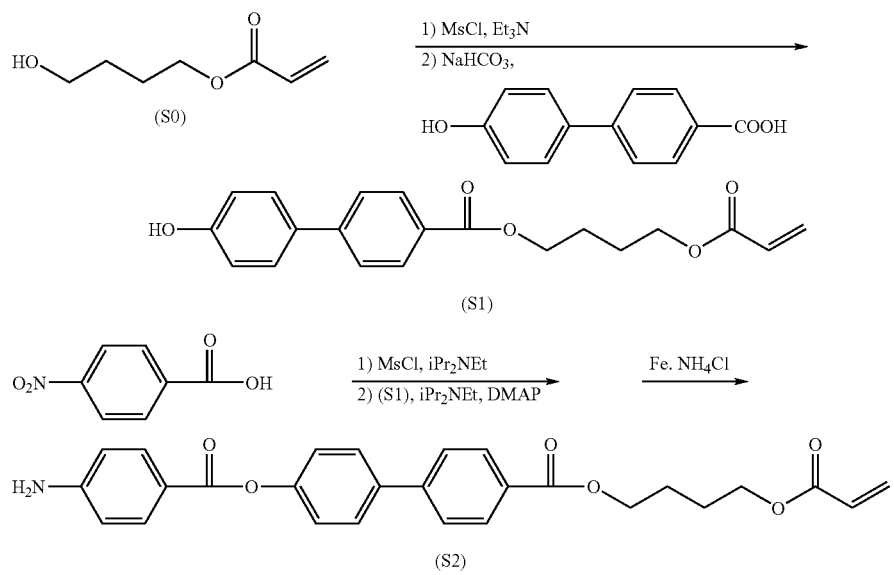

-continued

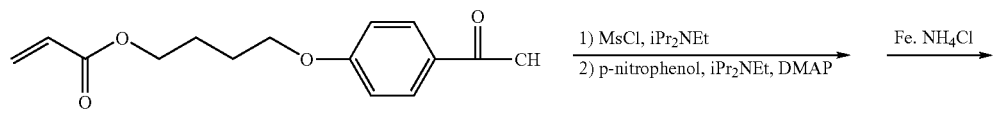

(S3)

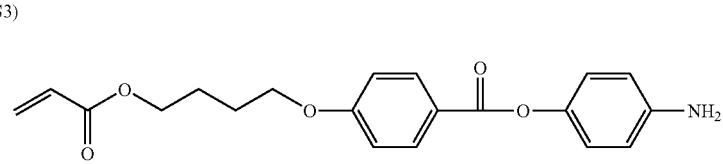

(S-4)

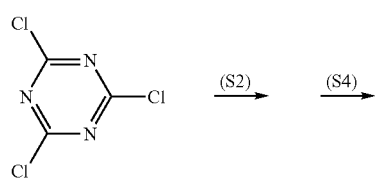

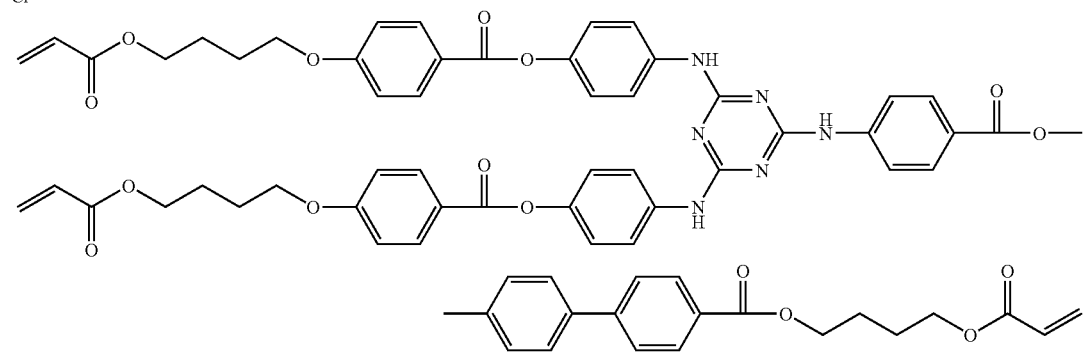

Exemplary Compound (14)

The Exemplary Compound (14) was synthesized using compounds S-2 and S-4, according to the synthetic route shown in the above.

Twenty-five milliliter of N-methyl pyrrolidone (NMP) containing 0.738 g (4.0 mmol) of cyanuric chloride was cooled to −5° C. in ice/methanol under stirring, and 10 ml NMP solution containing 1.93 g (4.2 mmol) of intermediate S2 was slowly dropped thereinto, while keeping the internal temperature at 0° C. After stirred at 0° C. for 30 minutes, 10 ml of NMP solution containing 2.99 g (8.4 mmol) of intermediate S3 was dropped thereinto, temperature of the reaction mixture was then elevated to room temperature, and successively to 100° C., and stirred at this temperature for 3 hours. Afterwards, the reaction mixture was cooled to room temperature, organic components were extracted into methylene chloride, the organic layer was washed successively with water and saturated brine, dried over magnesium sulfate, and then condensed under reduced pressure. The resultant mixture was purified by silica gel column chromatography (developing solvent: methylene chloride/methanol=50/1), to thereby obtain 1.0 g of Exemplary Compound (14) (yield 20%).

The product was found to show a melting point of 157° C., and a phase transition temperature from the crystal phase (Cr) to the smectic-A phase (SmA) of 157° C. General phase transition is observed as SmA-->nematic phase (N)-->isotropic phase (Iso) as the temperature elevates, whereas Exemplary Compound (14) began to polymerize at 180° C., so that temperatures of phase transitions SmA-->N and N-->Iso could not be measured.

[Exemplary Synthesis: Synthesis of Exemplary Compound (13)]

Exemplary compound (13) was similarly synthesized, according to the following scheme.

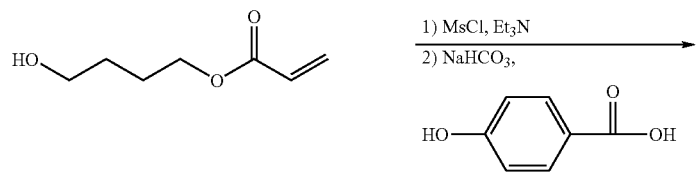

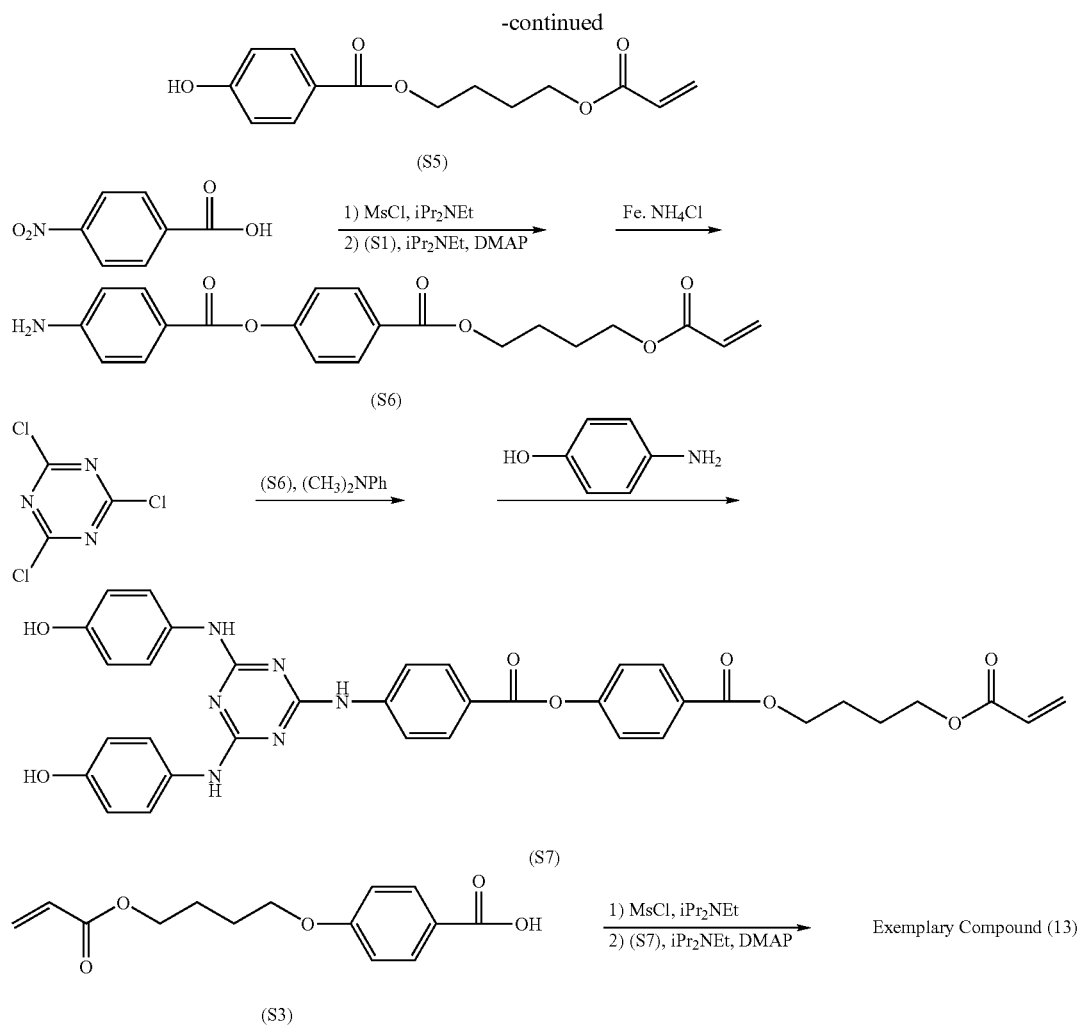

Synthesis of Intermediate (S7)

To 26 ml of DMAc dissolved with 1.38 g (7.5 mmol) of cyanuric chloride, 10 ml of DMAc containing 3.16 g (8.25 mmol) of intermediate (S6) dissolved therein was dropped, while cooling the mixture at −5° C. or below. To the mixture, 2.08 ml (16.5 mmol) of N,N-dimethyl aniline was then dropped, and the mixture was stirred at 0° C. or below for 1 hour. The mixture was then added with 1.80 g (16.5 mmol) of 4-aminophenol, and the reaction solution was stirred under heating at 80° C. for 2 hours. The reaction solution was then poured into 100 ml of water, and the product was extracted into methylene chloride. The organic layer was successively washed with a 1N hydrochloric acid, aqueous sodium hydrogen carbonate solution and saturated brine, dried over magnesium sulfate, and the solvent was removed under reduced pressure. The residual oily matter was recrystallized to yield 3.85 g of intermediate (S7).

Synthesis of Exemplary Compound (13)

To 40 ml of tetrahydrofuran dissolved with 3.91 g (14.8 mmol) of compound (S3), 0.96 ml (14.8 mmol) of methanesulfonyl chloride was dropped, while cooling the mixture at −5° C. or below. Then, 2.83 ml (16.3 mmol) of diisopropyl ethylamine was dropped thereinto, and the mixture was stirred at 0° C. for 30 minutes. The mixture was again cooled to −5° C. or below, and 30 ml of tetrahydrofuran dissolved with 3.85 g (5.7 mmol) of intermediate (S7) was dropped thereinto. Then, 2.58 ml (14.8 mmol) of diisopropyl ethylamine was dropped thereinto, the mixture was added with 181 mg (1.48 mmol) of 4-dimethylaminopyridine, and the mixture was stirred at room temperature for 2 hours. The reaction solution was poured into 200 ml of water, and the resultant oily matter was collected by decantation. The oily product was recrystallized from acetonitrile/water, and further purified by silica gel column chromatography (developing solvent; methylene chloride/methanol=20/1), and recrystallized from methylene chloride/methanol, to thereby obtain 2.5 g of Exemplary Compound (13).

The obtained Exemplary Compound (13) was found to show a melting point of 155° C., and to show phase transition in the order of Cr-->N-->Iso, wherein temperature of phase transition Cr-->N was 155° C., and temperature of phase transition N-->Iso was 175° C.

The exemplary synthesis described in the above dealt with the compounds where each of —$SP^1$—$R^1$ and —$SP^2$—$R^2$ in formula (I) is a group below:

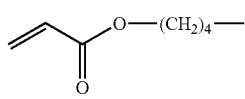

The compounds wherein the groups have different SP¹ and SP² may readily be synthesized by replacing the reagents S0 and S3 used in the above-described synthetic route with the following compounds:

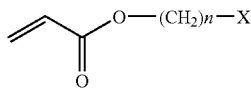

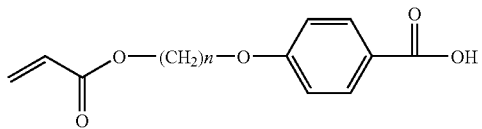

(in the formulae, X represents a halogen atom (preferably chlorine atom or bromine atom) or OH, and n represents an integer of 1 or larger); or

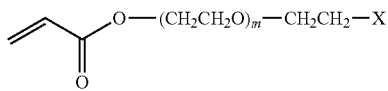

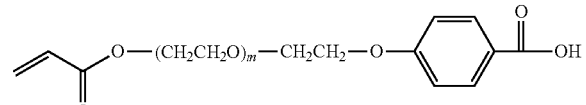

(in the formulae, X represents a halogen atom (preferably chlorine atom or bromine atom) or OH, and m represents an integer of 1 or larger).

Similarly, also compounds having substituted 1,4-phenylene groups for $M^{1a}$, $M^{1b}$ may readily be synthesized by a similar synthetic method, by replacing the compounds below used in the above-described
Exemplary Synthesis:

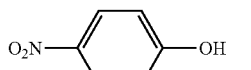 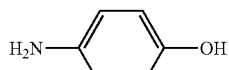

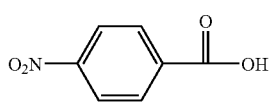

with the compounds having substituent(s) shown below:

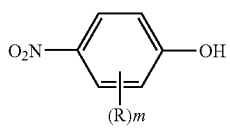 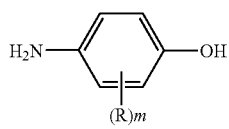

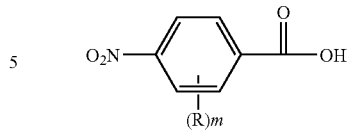

Similarly, also compounds having substituted aromatic rings for $M^{1b}$, $M^{2b}$ may readily be synthesized by using the compounds below:

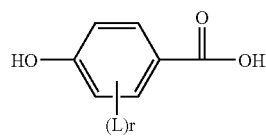

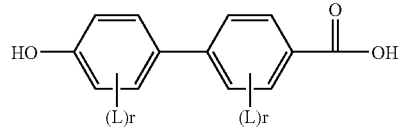

Example 2

<Producing Alignment Film>

To a surface of a cleaned glass substrate, a diluted solution of SE-150 from Nissan Chemical Industries, Ltd. was continuously applied, and the coated film was dried under hot air at 80° C. for 5 minutes, and then dried at 250° C. for 60 minutes, sintered to form a film, and the surface of the film was then rubbed to thereby obtain an alignment film.

<Producing Optically Anisotropic Film>

A 15% chloroform solution containing 50 parts by mass of Exemplary Compound (13), 50 parts by mass of Exemplary Compound (14), 2 parts by mass of polymerization initiator "Irgacure 819" (trade name, from Ciba Specialty Chemicals Inc.), and 0.2 parts by mass of an additive (Compound (I-6) described in JPA No. 2005-99248 shown below) mixed therein was prepared. The coating liquid was then applied to a surface of a slide glass, and observed under heating under a polarizing microscope. Temperature of phase transition from the smectic-A phase to the nematic phase was found to be 156° C., but temperature of phase transition from the nematic phase to the isotropic phase could not be measured, due to polymerization of the liquid crystal compound under heating. The coating liquid was applied to a surface of the alignment film according to a spin coating method, to thereby form a film. The film was then heated to a substrate temperature of 170° C., then cooled to 140° C. at a cooling rate of 5° C./min, and then irradiated by ultraviolet radiation at an energy of 1000 mJ/cm² so as to fix the state of alignment of the optically anisotropic layer, to thereby prepare an anisotropic material 1. Observation under a polarizing microscope showed a uniform alignment, with almost no defect. The material was found to have the slow axis in the direction of rubbing, wherein the retardation measured by Senarmont method was 200 nm at a wavelength of 546 nm. Thickness of the film herein was 1.5 μm.

Compound (I-6):

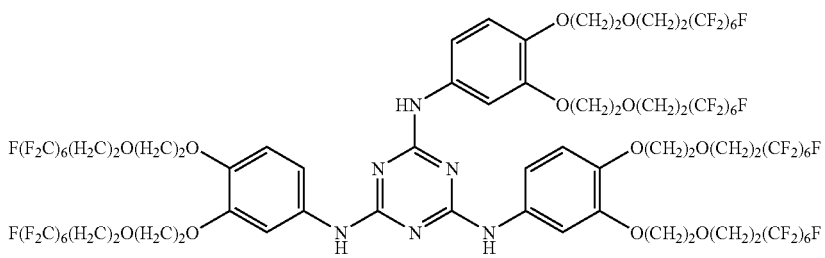

Example 3

<Producing Alignment Film>

To a surface of a cleaned glass substrate, a coating liquid for forming alignment film having the formulation below was applied in an amount of 20 ml/m², using a wire bar coater. The coated film was dried while being blown by hot air at 60° C. for 60 seconds, and further by hot air at 100° C. for 120 seconds, to thereby obtain an alignment film.

| Formulation of Coating Liquid for Forming Alignment Film | |
|---|---|
| Modified polyvinyl alcohol shown below | 10 parts by mass |
| Water | 371 part by mass |
| Methanol | 119 parts by mass |
| Glutaraldehyde | 0.5 parts by mass |

Modified polyvinyl alcohol

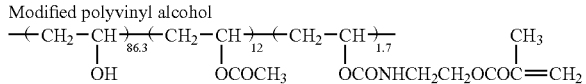

Onium salt

<Producing Optically Anisotropic Film>

A 15% chloroform solution containing 100 parts by mass of Exemplary Compound (13), 2 parts by mass of polymerization initiator "Irgacure 819" (trade name, from Ciba Specialty Chemicals Inc.), and 0.2 parts by mass of an additive (Compound (1-6) described in JPA No. 2005-99248) mixed therein was prepared. The coating liquid was spread on the alignment film by spin coating, to thereby form a film. The film was then irradiated by ultraviolet radiation at an energy of 1000 mJ/cm² at a substrate temperature of 110° C., so as to fix the state of alignment of the optically anisotropic layer, to thereby prepare an anisotropic material 2. Observation under a polarizing microscope showed a uniform alignment, with almost no defect. The material was found to have the slow axis in the direction of rubbing, wherein the retardation measured by Senarmont method was 142 nm at 546 nm. Thickness of the film herein was 0.8 μm.

Example 4

A 25% solution of 1,1,2-trichloroethane containing 50 parts by mass of Exemplary Compound (13), 50 parts by mass of Exemplary Compound (14), 1 part by mass of polymerization initiator "Irgacure 819" (trade name, from Ciba Specialty Chemicals Inc.), 2 parts by mass of the additive (1) shown below, and 0.2 parts by mass of the additive (2) below mixed therein was prepared. The coating liquid was then applied to a surface of a polyimide alignment formed on a glass plate, same as that used in Example 2, to thereby form a film. The film was heated to a substrate temperature of 170° C., cooled to 140° C. at a cooling rate of 5° C./min, and the irradiated with ultraviolet radiation at an energy of 1000 mJ/cm² so as to fix the state of alignment of the optically anisotropic layer, to thereby prepare an anisotropic material 4.

Additive (1)

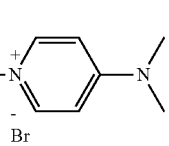

Additive (2)

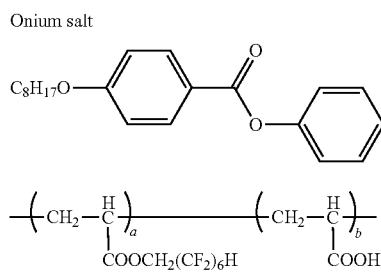

Observation under a polarizing microscope showed complete dark field of view, even when the rotary stage was rotated. Almost no optical anisotropy was observed in the normal direction. Measurement of dependence of Re of thus-produced film on the angle of incidence of light, using an automatic birefringence analyzer (KOBRA-21ADH, from Oji Scientific Instruments), revealed that Re observed in the normal direction was almost zero, whereas retardation measured at 40' was 40 nm at 589 nm, and retardation measured at −40° was 41 nm at 589 nm. And it is revealed that the obtained film was an optically anisotropic film having the slow axis in the vertical direction. Thickness of the film herein was 1.5 μm.

Comparative Example 1

The compound (B-7) below, described in JPA No. 2006-89672, was synthesized according to the method described in this publication, and the liquid crystallinity thereof was examined. The compound showed a melting point of 88° C. and the isotropic phase; but showed no liquid crystallinity.

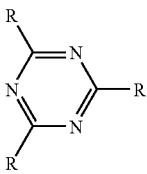

R =

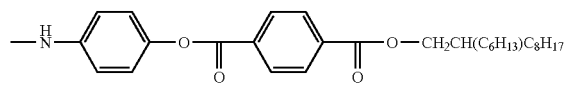

Compound (B-7) described in Japanese Laid-Open Patent Publication No. 2006-89672

Comparative Example 2

Comparative Compound (I) below was synthesized, and liquid crystallinity thereof was examined. The melting point was found to be 176° C., and showed phase transition in the order of Cr-->N-->Iso as the temperature elevated. Temperature of phase transition Cr-->N was found to be 176° C., and temperature of phase transition N-->Iso was found to be 216° C.

Comparative Compound (1)

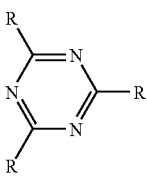

R =

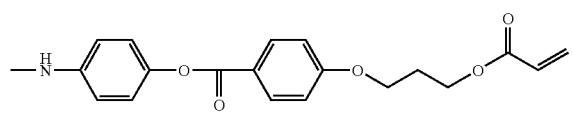

An optically anisotropic film was manufactured similarly to as described in Example 4, except that the Comparative Compound (I) shown in the above was used in place of Exemplary Compounds (13) and (14) used in Example 4. Thickness of thus-obtained optically anisotropic film was found to be 1.4 μm.

Observation of thus-obtained optically anisotropic film under a polarizing microscope showed almost complete dark field of view, even when the rotary stage was rotated, but showed non-uniformity in the alignment with a partial defect.

What is claimed is:

1. A triazine derivative represented by Formula(III) below:

Formula (III)

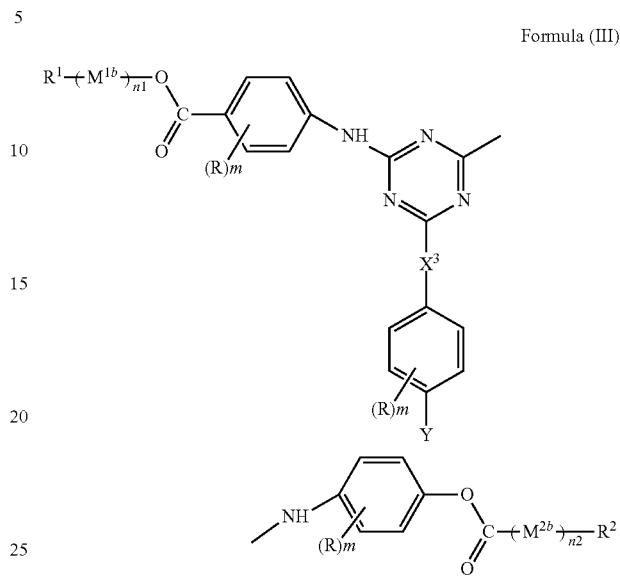

wherein, in the formula, each of $M^{1b}$ and $M^{2b}$ is a divalent group comprising one or more substituted or non-substituted aromatic rings; each of $R^1$ and $R^2$ represents a hydrogen atom or substituent; each of n1 and n2 is 0 or 1; $X^3$ represents a single bond, NH, S or O; each of Y and R represents a substituent; each m represents an integer from 0 to 4; and each of a plurality of (R)s and (m)s may be same or different from each other.

2. The triazine derivative of claim 1, wherein each of n1 and n2 is 1, and each of $M^{1b}$ and $M^{2b}$ is a group comprising at least one substituted or non-substituted 1,4-phenylene group.

3. The triazine derivative of claim 1, wherein each of $R^1$ and $R^2$ comprises a polymerizable group represented by any of formulae (Q-101) to (Q-106) below:

(Q-101)

(Q-102)

(Q-103)

(Q-104)

-continued (Q-105)

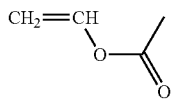

(Q-106)

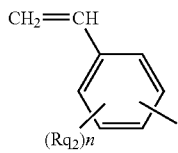

where, in the formulae, $Rq_1$ is a hydrogen atom, alkyl group, or aryl group; $Rq_2$ is a substituent; and n is an integer from 0 to 4.

4. The triazine derivative of claim 1, wherein Y in said formula (III) is either of the formulae below;

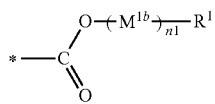 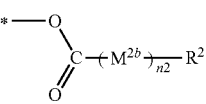

where, in the formula, each of $M^{1b}$, $M^{2b}$, $R^1$, $R^2$, n1 and n2 is synonymous with each of those in formula (I), and * indicates a binding site to benzene ring.

5. The triazine derivative of claim 1, wherein $-(M^{1b})_{n1}-R^1$ is a group represented by formula (I)-1 below, and $-(M^{2b})_{n2}-R^2$ is a group represented by formula (I)-2 below:

$-(Ph^1-L^1)_{m1}-X^1—SP^1-Q$   Formula (I)-1

$-(Ph^2-L^2)_{m2}-X^2—SP^2-Q$   Formula (I)-2 wherein in the formulae, each of $Ph^1$ and $Ph^2$ represents a substituted or non-substituted 1,4-phenylene group; $L^1$ represents a single bond or #—C(=O)O— (# indicates a binding site to $Ph^1$); $L^2$ represents a single bond or #—OC(=O)— (# indicates a binding site to $Ph^2$); each of m1 and m2 is an integer from 1 to 3, and each of m1 $(Ph^1-L^1)$s and m2 $(Ph^2-L^2)$s may be same with or different from each other; each of $SP^1$ and $SP^2$ represents a spacer group comprising a chain structure having four or more atoms; each of $X^1$ and $X^2$ represents a single bond or divalent linking group; and Q represents any of the polymerizable groups represented by formulae (Q-101) to (Q-106) in claim 5.

6. The triazine derivative of claim 1, having liquid crystallinity.

7. The triazine derivative of claim 6, having a smectic phase.

8. The liquid crystal composition comprising at least one triazine derivative as set forth in claim 1.

9. An anisotropic material formed by curing a liquid crystal composition as set forth in claim 8.

10. A liquid crystal display device comprising an anisotropic material as set forth in claim 9.

* * * * *